US008877222B2

(12) United States Patent
Aizawa et al.

(10) Patent No.: US 8,877,222 B2
(45) Date of Patent: Nov. 4, 2014

(54) ANTIBACTERIAL MEDICAL EQUIPMENT AND METHOD FOR PRODUCING THE SAME

(75) Inventors: Mamoru Aizawa, Kawasaki (JP);
Tomoyuki Hoshikawa, Kamagaya (JP);
Ken Ishii, Tokyo (JP); Haruki Funao,
Tokyo (JP)

(73) Assignees: Meiji University, Tokyo (JP); Keio University, Tokyo (JP)

( * ) Notice: Subject to any disclaimer, the term of this patent is extended or adjusted under 35 U.S.C. 154(b) by 0 days.

(21) Appl. No.: 13/321,215

(22) PCT Filed: May 19, 2010

(86) PCT No.: PCT/JP2010/058867
§ 371 (c)(1),
(2), (4) Date: Nov. 18, 2011

(87) PCT Pub. No.: WO2010/134638
PCT Pub. Date: Nov. 25, 2010

(65) Prior Publication Data
US 2012/0064132 A1 Mar. 15, 2012

Related U.S. Application Data

(60) Provisional application No. 61/272,498, filed on Sep. 30, 2009.

(30) Foreign Application Priority Data

May 20, 2009 (JP) ................................. 2009-122472

(51) Int. Cl.
| A61F 2/00 | (2006.01) |
| A61K 33/42 | (2006.01) |
| A61K 33/38 | (2006.01) |
| A61K 33/06 | (2006.01) |
| A61L 31/16 | (2006.01) |
| A61L 27/54 | (2006.01) |
| A61L 31/02 | (2006.01) |
| A61L 29/02 | (2006.01) |
| A61L 29/16 | (2006.01) |
| A61L 27/12 | (2006.01) |

(52) U.S. Cl.
CPC ........... *A61L 27/12* (2013.01); *A61L 2300/104* (2013.01); *A61L 31/16* (2013.01); *A61L 2300/404* (2013.01); *A61L 27/54* (2013.01); *A61L 31/026* (2013.01); *A61L 2300/606* (2013.01); *A61L 29/02* (2013.01); *A61L 29/16* (2013.01)
USPC ............................ 424/422; 424/602; 424/618

(58) Field of Classification Search
None
See application file for complete search history.

(56) References Cited

U.S. PATENT DOCUMENTS

2002/0099449 A1   7/2002 Speitling

2008/0306554 A1   12/2008 McKinley
2009/0324684 A1*  12/2009 Atanasoska et al. .......... 424/426
2010/0136083 A1*  6/2010 Prentice et al. ............... 424/423

FOREIGN PATENT DOCUMENTS

| JP | 11-116413 | | 4/1999 |
| JP | 2004-002227 | * | 1/2004 |
| JP | 2004-002227 A | | 1/2004 |
| JP | 2005-095346 A | | 4/2005 |
| JP | 2006150274 A | | 6/2006 |
| JP | 2008074786 A | | 4/2008 |
| JP | 2008200476 A | | 9/2008 |
| WO | 2007-085852 A2 | | 8/2007 |
| WO | 2008081861 A1 | | 7/2008 |
| WO | 2008090648 A1 | | 7/2008 |

OTHER PUBLICATIONS

Hoppenbrouwers, P.M.M., et al. (Adherence of Oral Bacteria to Chemically Modified Hydroxyapatite, Caries Res. 18: 1-6 (1984)).*
Machine translation of Yamaguchi (JP 2004-002227, cited on Dec. 16, 2013 IDS).*
Aizawa M. et al., Surface modification of hydroxyapatite ceramics by inositol phosphate and its evaluation by cell culture, Preprints of 13th Fall Meeting of The Ceramic Society of Japan, Oct. 11, 2000, p. 90.
Haruta Y. et al., Surface analysis of surface modification of hydroxyapatite ceramics by inositol phosphate and its evaluation by cell culture, Preprints of Annual Meeting of The Ceramic Society of Japan, Mar. 21, 2001, p. 277.
International Search Report issued in PCT application No. PCT/JP2010/058867, dated Aug. 10, 2010, 2 pages.
Japanese Patent Office, Office Action issued in Application No. 2009-122472, mailed Sep. 17, 2013, 9 pp.
European Patent Office, extended European Search Report issued in corresponding European Patent Application No. 10777865.6 (Apr. 9, 2014) (7 pages).

* cited by examiner

*Primary Examiner* — Robert A Wax
*Assistant Examiner* — H. Sarah Park
(74) *Attorney, Agent, or Firm* — Wood, Herron & Evans, LLP

(57) ABSTRACT

An object of the present invention is to provide an antibacterial medical equipment which has sufficient antibacterial activity in vivo and is excellent in compatibility with living tissues, and also can maintain antibacterial activity over a long period and has high safety.
An antibacterial medical equipment characterized in that inositol phosphate is bonded to a Ca compound of a medical equipment whose surface is at least coated with a layer of the Ca compound, or a medical equipment comprising the Ca compound. The antibacterial medical equipment as described above, wherein silver ions are bonded to the inositol phosphate. A method for producing an antibacterial medical equipment, which comprises bringing a medical equipment whose surface is at least coated with a layer of a Ca compound, or a medical equipment comprising a Ca compound into contact with an aqueous solution of inositol phosphate to obtain an antibacterial medical equipment in which inositol phosphate is bonded to the Ca compound. The method for producing an antibacterial medical equipment, wherein inositol phosphate is bonded to the Ca compound and then the Ca compound is brought into contact with an aqueous solution containing silver ions to obtain an antibacterial medical equipment in which silver ions are bonded to the inositol phosphate.

8 Claims, 27 Drawing Sheets

(a)

(b)

(c)

(a) ×500

(b) ×5000

(c) ×10000

(d) ×20000

(e)

ANTIBACTERIAL MEDICAL EQUIPMENT AND METHOD FOR PRODUCING THE SAME

PRIORITY CLAIM

This application claims priority on Japanese Patent Application No. 2009-122472 filed on May 20, 2009 in Japan and U.S. Patent Application No. 61/272,498 filed on Sep. 30, 2009 in USA, the disclosure of which is incorporated by reference herein.

TECHNICAL FIELD

The present invention relates to medical equipments such as an implant and a surgical instrument used in the medical field, and more particularly to an antibacterial medical equipment having antibacterial activity, and a method for producing the same.

BACKGROUND ART

Conventionally, a technology disclosed, for example, in WO 2008/081861 has been proposed as a technology for a titanium-based or non-titanium based member having antibacterial activity in an implant.

WO 2008/081861 discloses an antibacterial member coated with titanate, including a substrate, a layer of a nanosheet, nanotube, nanofiber or nanocrystal made of a crystalline alkali titanate formed on the substrate, and a silver titanate layer in which a portion or all of an alkali component of the alkali titanate is substituted with silver ions.

WO 2008/081861 also discloses, as a method for producing the antibacterial member, the method comprising the steps of (i) subjecting a titanium-based substrate to a hydrothermal treatment in an aqueous alkali solution at a temperature of 110 to 180° C., (ii) heat-treating the product after subjecting to the hydrothermal treatment at 200 to 700° C., and (iii) washing and drying the product after subjecting to the heat treatment, and immersing the product in an aqueous silver ion-containing solution.

Since the antibacterial member disclosed in WO 2008/081861 includes the silver titanate layer, high antibacterial activity is obtained. However, there was a problem in that when this antibacterial member is used in an implant, titanate or silver titanate makes contacted with living tissues, resulting in poor compatibility between the implant and living tissues.

In the silver titanate layer of the antibacterial member, since a portion or all of the alkali component of the alkali titanate is substituted with silver ions, the degree of elution of silver ions varies drastically depending on a usage state of an implantation site, as described in Example 10. Therefore, this antibacterial member may not exhibit antibacterial activity when silver ions are not eluted, or exhibit toxicity when silver ions are excessively eluted. Also, there may arise a problem that antibacterial activity cannot be maintained over a long period because the degree of elution of silver ions is unstable.

DISCLOSURE OF INVENTION

Under these circumstances, the present invention has been made and an object thereof is to provide an antibacterial medical equipment which has sufficient antibacterial activity in vivo and is excellent in compatibility with living tissues, and also can maintain antibacterial activity over a long period and has high safety.

In order to achieve the above object, the present invention provides an antibacterial medical equipment characterized in that inositol phosphate is bonded to a Ca compound of a medical equipment whose surface is at least coated with a layer of the Ca, or a medical equipment comprising the Ca compound.

The antibacterial medical equipment of the present invention may have a constitution such that silver ions are bonded to the inositol phosphate.

The inositol phosphate is preferably phytic acid (inositol hexaphosphate, hereinafter sometimes abbreviated to $IP_6$).

The Ca compound is preferably hydroxyapatite (hereinafter referred to as HAp).

The antibacterial medical equipment is preferably an antibacterial implant.

The present invention provides a method for producing an antibacterial medical equipment, which comprises bringing a medical equipment whose surface is at least coated with a layer of a Ca compound layer, or a medical equipment comprising a Ca compound into contact with an aqueous solution of inositol phosphate to obtain an antibacterial medical equipment in which inositol phosphate is bonded to the Ca compound.

In the method for producing an antibacterial medical equipment of the present invention, it is also possible to obtain an antibacterial medical equipment in which silver ions are bonded to the inositol phosphate by bonding inositol phosphate to the Ca compound and bringing the Ca compound into contact with an aqueous solution containing silver ions.

The inositol phosphate is preferably phytic acid.

The Ca compound is preferably HAp.

The antibacterial medical equipment is preferably an antibacterial implant.

According to the antibacterial medical equipment of the present invention, since inositol phosphate is bonded to a Ca compound of a medical equipment whose surface is at least coated with a layer of the Ca compound, or a medical equipment comprising the Ca compound, it is possible to provide an antibacterial medical equipment which has sufficient antibacterial activity in vivo and is excellent in compatibility with living tissues, and also can maintain antibacterial activity over a long period and has high safety.

When the antibacterial medical equipment of the present invention has a constitution such that silver ions are bonded to the inositol phosphate, it is possible to provide an antibacterial medical equipment having more instantaneous antibacterial activity.

According to the method for producing an antibacterial medical equipment of the present invention, since an aqueous solution of inositol phosphate is brought into contact with the Ca compound of a medical equipment to obtain an antibacterial medical equipment in which inositol phosphate is bonded to the Ca compound, it is possible to provide an antibacterial medical equipment which has sufficient antibacterial activity in vivo and is excellent in compatibility with living tissues, and also can maintain antibacterial activity over a long period and has high safety, efficiently at low cost.

According to the method for producing an antibacterial medical equipment of the present invention, since inositol phosphate is bonded to the Ca compound and then the Ca compound is brought into contact with an aqueous solution containing silver ions to obtain an antibacterial medical equipment in which silver ions are bonded to the inositol phosphate, it is possible to produce an antibacterial medical equipment having more instantaneous antibacterial activity, efficiently at low cost.

BRIEF DESCRIPTION OF THE DRAWINGS

FIG. 5 shows a process for preparation of titanium-based substrate in Examples, in which FIG. 5(a) is an enlarged image of a surface of titanium after surface polishing, FIG. 5(b) is a graph showing measurement results by EDX of elements contained in the surface, and FIG. 5(c) is an image of titanium subjected to an polishing treatment (left) and an image of untreated titanium (right).

FIG. 7 is a SEM image of a surface of HAp-coated titanium, in which FIG. 7(a) is an image magnified 500 times, FIG. 7(b) is an image magnified 5,000 times, FIG. 7(c) is an image magnified 10,000 times, FIG. 7(d) is an image magnified 20,000 times, and FIG. 7(e) is a graph showing measurement results of elements contained in the same surface.

Enzyme-linked immunosorbent assay (ELISA) method was used for measurement of the level of two inflammatory molecules.

Figure 36:
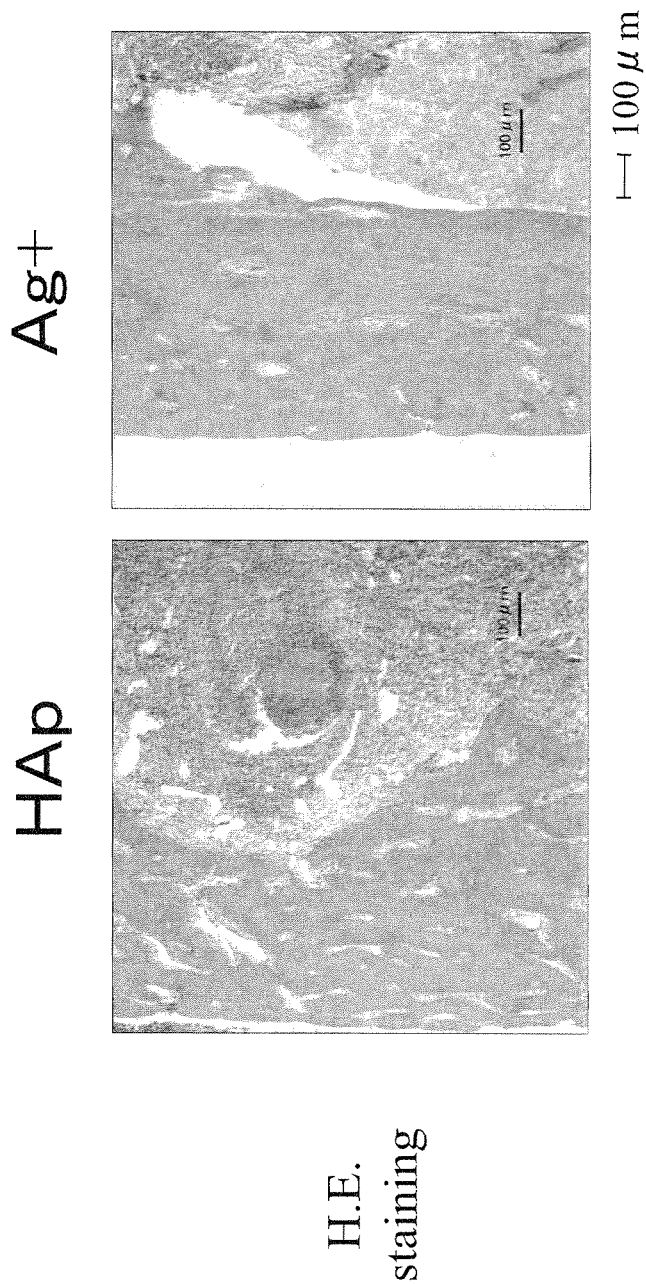

FIG. 36 shows Hematoxylin and eosin (HE) staining of histological sections from thighbones collected at 4 weeks after implantation in both groups.

Figure 37:
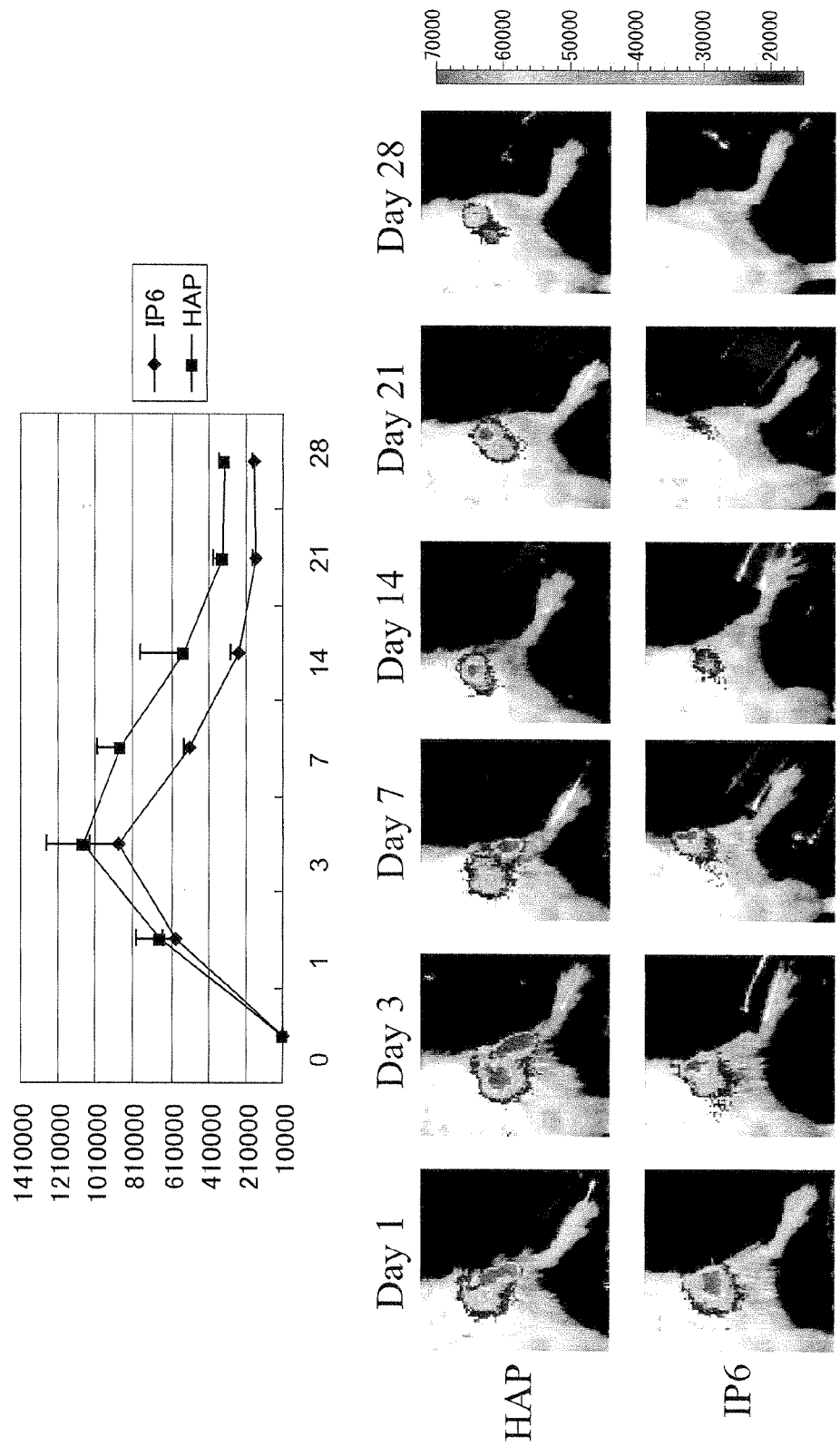

FIG. 37 shows a graph and bluc images, revealing time course results of a bacterial growth around an implant in a mouse in an in vivo test-2 in which implant samples No. 4 and No. 5 are implanted to the thighbone, followed by an injection of *Staphylococcus aureus*.

EXEMPLARY EMBODIMENT FOR CARRYING OUT THE INVENTION

Embodiments of the present invention will be described below with reference to the accompanying drawings.

In the present invention, the "medical equipment" includes medical equipments defined in Pharmaceutical Affairs Act revised in 2002. Among such medical equipments, a medical equipment made of metallic materials such as pure titanium, titanium alloy (Ti-6Al-4V alloy, etc.), stainless steel, low carbon steel, copper or copper alloy, silver or silver alloy, gold or gold alloy, platinum group elements such as platinum or alloy thereof, and cobalt-chromium alloy; a medical equipment made of synthetic resins such as polyether ether ketone (PEEK), carbon, carbon fiber-reinforced PEEK, polyethylene, polypropylene, polyethylene terephthalate (PET), fluororesin, silicone resin, and polylactic acid; a medical equipment made of Ca compounds such as HAp; and a medical equipment made of ceramics such as silica, alumina, and zirconia are preferred. The "medical equipment" of the present invention is also applied to tableware and toys which are desirably imparted with antibacterial activity.

Preferred medical equipment in the present invention will be exemplified below.

[Implants which can be Subjected to an Antibacterial Treatment]

Tubes: tracheostomy tube, tracheal tube, tube for ileus, tympanostomy tube, tube for control of bleeding from esophagogastric varices, shunt tube, vascular tube, urination tube, various drainage tubes, continuation tube, etc.;

Catheters: catheter for measurement of arterial or venous pressure, thermodilution catheter, catheter for collection of blood in coronary sinus, angiographic catheter, blood vessel endoscope catheter, rectal catheter, central vein catheter, trochar catheter, nutrition catheter, stomach tube catheter, suction indwelling catheter, nephrostomy catheter, cystostomy catheter, catheter for percutaneous or endoscopic naso-biliary drainage, gastrostomy catheter, indwelling bladder catheter, intravenous catheter for blood access, peritoneum dialysis catheter, catheter for treatment of sinusitis, medullary cavity catheter for implantable infusion pump, percutaneous catheter, catheter for myocardial ablation, balloon catheter for balloon pumping, catheter for cardiac surgery, guiding catheter, catheter for intravascular operation, catheter for urinary tract dilatation, catheter for removal of biliary stone, catheter for removal of renal or ureteral stone, drain catheter, catheter for measurement of cardiac output volume, catheter for measurement of cerebrospinal fluid pressure, catheter for diagnostic imaging, digestive organ internal-pressure catheter, catheters for abdominal angiography, catheter for multipurpose imaging, catheter for digestive organ imaging, catheter for endoscopic imaging, catheter for cervical cerebrospinal angiography, catheter for cardiac and thoracic angiography, electrode catheter, PTCA catheter, uterus or oviduct catheter, urethral catheter, catheter for measurement of urethal internal pressure or intravesical pressure, ureteral catheter, balloon catheter, catheter for removal of ureteral stone, indwelling catheter, suction catheter, etc.;

Guide wires, wires: guide wire for catheter for percutaneous transluminal coronary angioplasty, guide wire with a sensor for coronary angiography, guide wire for angiography, guide wire for catheter for valve extension, heart-implantable wire for external pacemaker, metal wire for spinal surgery, PTCA guide wire, Kirschner wire, etc.;

Needles: plastic cannula type intravenous indwelling needle, cerebrospinal cannula, needle for cervical cerclage, butterfly needle, needle for cardiac surgery, needle for angiography, long needle, spinal needle, etc.;

Electrodes: catheter electrode for implantable cardiac defibrillator, electrode for body surface pacing, catheter electrode for external pacemaker, implantable cerebrospinal electrostimulator, intracranial electrode for measurement of brain wave, lead for implantable cardiac pacemaker, etc.;

Intravascular ultrasonic wave probes;

Dilators: blood vessel dilator, urethral or renal dilator, muscular dilator, etc.;

Clips: clip for surgery of cerebral arterial aneurysm, clip for blocking of brain blood, clip for surgery of cerebral arteriovenous malformation, clip for dura damage, clip for vascular surgery, WECK clip, auto-inosculating or auto-suture appliance, hemostatic or ligature clip, vessel clamp, etc.;

Artificial membranes, artificial fibers: artificial dura, artificial textile fabric substituted for tissue, synthetic resorbable adhesion barrier, wound dressing material for skin loss defect, graft for dermis loss defect, etc.;

Stents: biliary stent, ureteral stent, urethral stent, tracheobronchial stent, esophageal stent, aortic stent graft, coronary stent, umbrella for prevention of pulmonary embolism, etc.;

Internal fixation materials: splint (plate), internal splint for fixation (screw), internal splint for fixation (plate), internal splint for fixation of outer the thighbone, washers or nuts for internal splint for fixation, external fixation implant, intramedullary nail, fixation nail, fixation metal wire, fixation metal pin, absorbable pin or screw, etc.;

Materials for fixation of backbone: pyramidal washer, backbone rod, backbone plate, pyramidal hook, backbone screw, backbone connector, backbone wire, Nesplon tape, etc.;

Intervertebral spacer's (cages);

Artificial joints: artificial hip joint, artificial knee joint, artificial shoulder joint, artificial elbow joint, artificial wrist joint, artificial ankle joint, artificial finger joint, custom made artificial joint, etc.;

Artificial organs: artificial cardiopulmonary bypass system, artificial blood vessel, artificial pharynx, material for artificial inner ear, artificial ligament, artificial femoral head cap, artificial bone, custom made artificial bone, mechanical valve, biological valve, graft with valve (biological valve), artificial valve annulus, cardiac valve, auxiliary artificial heart, disposable artificial lung (model lung), artificial lung, artificial gullet, artificial breast, implant for urology department, otolaryngological prosthesis, etc.;

Pacemakers;

Cardiac defibrillators: implantable cardiac defibrillator, implantable cardiac defibrillator with the function of biventricular pacing, etc.;

Leads: lead for deep brain stimulator, lead for spinal cord stimulator, etc.;

Otolaryngology-related medical materials: lacrimal opening plug, nasal septum prosthesis, nare prosthesis, etc.;

Hemostatic materials: gelatin sponge hemostatic material, dextranomer, fibrillary collagen, puncture site hemostatic material for percutaneous transluminal coronary angioplasty, etc.;

Valves: cranial, venous or abdominal shunt valve, pleural effusion or ascitic fluid shunt valve, etc.;

Pumps: implantable infusion pump, centrifugal blood pump for extracorporeal circulation, pump for intraspinal continuous infusion, etc.;

Cannulas: cannula for extracorporeal circulation;

Filters: blood filter for blood transfusion, filter for anesthesia apparatus or artificial respirator, etc.;

Embolism substances: hepatic arterial embolism substance, brain surgical platinum coil, etc.;

Endoscopes;

Syringes: insulin preparation syringe, human growth hormone drug syringe, hormone preparation syringe, injection needle for fountain-pen syringe, etc.;

Machines and devices: plasma separator for plasma exchange, plasma component separator for plasma exchange, tissue expander, adsorptive blood purifier (for removal of endotoxin), dedicated circuit of peritoneal dialyzer, ascitic fluid filter (including circuit), concentrator for concentrated ascites reinfusion (including circuit), etc.;

Others: bone cement, synthetic absorbable bone chip bonding material, pin hammer for urinary tract lithotripsy treatment system, none-adherent silicone gauze, material for centrifugal removal of leukocytes, material for adsorption of leukocytes, circulating sorption column for artificial kidney, dust mat, operating table, operating table-related appliances, etc.;

Drains: drain catheter, drain vessel, etc.;

Bags: urine bag, postoperative drain bag, etc.; and

Drapes: surgical plastic drain, etc.

[Surgical Instruments]

Scalpels;

Forceps: gullet forceps, bone clamping forceps, right angle forceps, abortion forceps, intestinal forceps, hemostatic forceps, artery forceps, towel forceps for scalp, ablation forceps, thread forceps, bulldog forceps for implantation, Fogarty blood vessel forceps, hemoclip forceps, gastric forceps, Lister forceps, caval forceps, duodenal forceps, bone forceps, stump appendix forceps, arthrosis forceps, tendon inducing forceps, thyroid forceps, lymphatic gland forceps, pleurolysis forceps, bone rongeur forceps, babcock forceps, multipurpose blood vessel forceps, curette forceps, connective tissue compressive forceps, mosquito forceps, Küstner uterine safety forceps, blood vessel forceps, Pean forceps, Martin tenaculum forceps, drain forceps, Kocher's forceps, Muzeaux tenaculum forceps, Melabulldog forceps, Kelly's forceps, forceps with shank, thoraco- or laparo-scopic forceps forceps, Allis forceps, Bulldog forceps, Mikulicz forceps, towel forceps, placenta forceps, etc.;

Scalpel holders;

Elevatoriums;

Raspatriums;

Hammers;

Rongeurz;

Spatulas: enteric spatula, cerebral spatula, nervous spatula, etc.;

Luer;

Tweezers;

Retractors: Adson, Gelpi, Weitlaner, etc.;

Mouth gags;

Retractors: muscle retractor, Tensho type sharp retractor, nerve retractor, lung hemorrhage retractor, saddle retractor, extra-large width vastus muscle retractor, Diva retractor, Hohmann retractor, scapula retractor, ureteral retractor, tendon traction retractor, maxillary sinuses retractor, flat retractor, demar retractor, etc.;

Kerrisons;

Scissors: ophthalmic scissors, plastic surgery scissors, scanlan scissors, backward rib scissors, etc.;

Drills;

Needle holders: Mathieu, Scamed, Sarot, Rider, Webster, Sweden, etc.;

Spreaders;

Hooks: skin hook, French hook, etc.;

Clips: Lenin Clip, etc.;

Towels: cup, etc.;

Retractors;

Metal Petri dishes;

Threads;

Masks (for doctor, nurse, for ventilation of patients;

Gloves;

Surgical gowns;

Gauzes;

Needles: injection needle, aneurysm needle, cerebral ventricles tap needle, Deschamps aneurysm needle, etc.;

Sondes;

Beakers;

Trays;

Pus basins;

Curettes: soft curette, dental bone curette;

Rasoriums: dental rasorium, nerve rasorium, oral cleft rasorium, otolaryngological rasorium, etc.;

Endoscopes: anal speculum, skull endoscope, nasal speculum, vaginal speculum, aural speculum, arthroscope, rectal speculum, capsule endoscope, etc.;

Forceps: blood vessel forceps, Sweden forceps, Bergh forceps, microforceps, otolaryngological forceps, cushing forceps, dental forceps, hook forceps, bent nose DeBakey forceps long forceps, Adson forceps, Prince forceps, etc.;

Tongue depressors;

Suction tubes;

Files;

Mirrors;

Stethoscopes;

Scissors: Cooper, Mecchen, etc.; and

Scissors

[Others]

Toilet stools;

Washstands;

Handrails;

Parts inside computers;

Clinical thermometers;

Appliances for cosmetic surgery (for rhinoplasty, silicone for breast augmentation);

Various dental implants;

False teeth;

Contact lens; and

Some industrial equipment.

Figure 1:
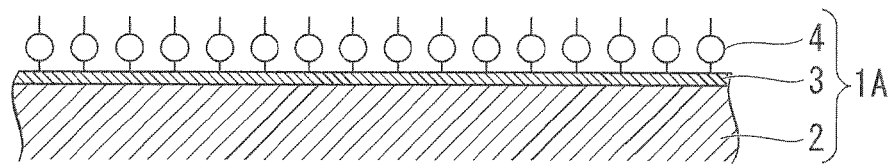
FIG. 1 is a schematic diagram showing the first embodiment of an antibacterial medical equipment of the present invention.

FIG. 1 is a schematic diagram showing the first embodiment of an antibacterial medical equipment of the present invention. An antibacterial medical equipment 1A of the present embodiment has a structure in which a HAp layer 3 as a Ca compound layer is formed on a surface of a medical equipment 2 made of a material other than a Ca compound and inositol phosphate 4 is bonded to the HAp layer 3.

The HAp layer 3 is made of HAp represented by $Ca_{10}(PO_4)_6(OH)_2$ or made of HAp in which a molar ratio of each constituent element slightly varies and a trace amount of carbonate ions is contained, and at least one portion, preferably all of a surface of the medical equipment 2 is coated with the HAp layer. The thickness of this HAp layer 3 is preferably 1 μm or more. The Ca compound layer is not limited to this HAp layer 3 and another insoluble Ca compound, for example, octacalcium phosphate, calcium hydrogen phosphate, calcium sulfate, calcium carbonate, and insoluble salts in which a portion of Ca is substituted with Mg may also be used.

There is no particular limitation in the method for formation of the HAp layer 3 and the method includes, for example, a dry film formation method such as a plasma spraying method, a vacuum deposition method, or a chemical vapor phase deposition (CVD) method; and a wet method such as a method in which HAp is precipitate/adhered on a surface of a medical equipment 2 in an aqueous solution containing a Ca compound and a P compound. Among these methods, the wet method is preferred because it can be applied to the medical equipment 2 made of various materials and also a HAp layer 3 can be formed in abundance and at low cost. The wet method is particularly preferably a method in which urea and urease are added in a solution containing a Ca compound and a P compound dissolved therein in a ratio corresponding to a molar ratio of the composition of HAp and a medical equipment 2 is immersed in the mixed solution, and then incubation is conducted at a temperature of about 30 to 60° C., preferably about 50° C. thereby to precipitate HAp and to adhere the HAp to a surface of the medical equipment 2.

The inositol phosphate is inositol phosphate in which at least one of six hydroxyl groups of inositol (1,2,3,4,5,6-cyclohexanehexaol) is phosphorylated. In the present invention, the inositol phosphate is preferably inositol phosphate in which three or more of hydroxyl groups are phosphorylated, more preferably inositol phosphate in which four or more of hydroxyl groups are phosphorylated, and most preferably phytic acid (inositol hexaphosphate, $IP_6$ in which all hydroxyl groups of inositol are phosphorylated. Phytic acid has a strong chelate effect and exists in the state of being bonded to Ca ions of the HAp layer 3 in an antibacterial medical equipment 1A of the present embodiment.

As described above, the antibacterial medical equipment 1A of the present embodiment can be simply produced by forming the HAp layer 3 on a surface of the medical equipment 2 and immersing in a solution of inositol phosphate such as $IP_6$ thereby bonding inositol phosphate 4 to the HAp layer 3. It is also possible that an inositol phosphate solution is spray-coated on the surface of the HAp layer 3 instead of immersion in the inositol phosphate solution thereby bonding inositol phosphate to Ca on the surface.

Although it is predicted that inositol phosphate such as the phytic acid has an antitumor effect, regarding the in vivo effect thereof, sufficient elucidation of the detailed effect is not yet known.

On the other hand, in the present invention, we have already found new operational advantages such that inositol phosphate in the state of being bonded to a Ca compound of the HAp layer 3, and the like, has antibacterial activity.

In the antibacterial medical equipment of the present invention 1A, it is preferred to bond the inositol phosphate 4 to the Ca compound of the HAp layer 3 as much as possible. The amount of the inositol phosphate 4 bonded to the Ca compound can be appropriately adjusted by the concentration of or the time of immersion in inositol phosphate in the case of immersing the medical equipment 2 with the HAp layer 3 formed on the surface in a solution of the inositol phosphate 4.

The antibacterial medical equipment 1A of the present embodiment has a structure in which a HAp layer 3 as a Ca compound layer is formed on a surface of a medical equipment 2 and inositol phosphate 4 is bonded to the HAp layer 3, and has operational advantages such as antibacterial activity which could have never been predicted by conventional knowledge with respect to inositol phosphate. Thus, it is possible to provide an antibacterial medical equipment which has practically sufficient antibacterial activity and is excellent in compatibility with living tissues, and also can maintain antibacterial activity over a long period and has high safety.

Figure 2:
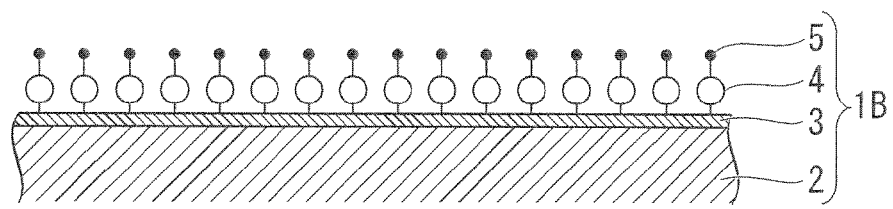
FIG. 2 is a schematic diagram showing the second embodiment of an antibacterial medical equipment of the present invention.

FIG. 2 is a schematic diagram showing the second embodiment of the antibacterial medical equipment of the present invention. The antibacterial medical equipment 1B of the present embodiment has a structure in which a HAp layer 3 as a Ca compound layer is formed on a surface of a medical equipment 2 made of a material other than a Ca compound and inositol phosphate 4 is bonded to the HAp layer 3, and also silver ions 5 are bonded to the inositol phosphate 4.

The inositol phosphate 4 bonded to the HAp layer 3 can still be chelate-bonded and silver ions 5 can be bonded to inositol phosphate 4 by bringing silver ions into contact with the inositol phosphate. Silver ions 5 bonded to the inositol phosphate 4 are gradually released by bringing into contact with body fluids and tissues in vivo and exert strong antibacterial activity.

The antibacterial medical equipment 1B of the present embodiment can be easily produced by immersing the above-described antibacterial medical equipment 1A of the first embodiment in an Ag ion-containing solution such as an aqueous $AgNO_3$ solution, followed by taking out, washing and drying, or spray-coating the solution, followed by washing and drying. There is no particular limitation on the amount of silver ions 5 bonded, and a proper amount of silver ions 5 may be bonded according to the kind of the antibacterial medical equipment 1B and purposes. The amount of silver ions 5 bonded can be appropriately adjusted by the concentration of silver ions used for immersion and the immersion time.

Since the antibacterial medical equipment 1B of the present embodiment has a structure in which silver ions 5 are bonded to the inositol phosphate 4 in the above-described antibacterial medical equipment 1A of the first embodiment, it is possible to provide an antibacterial medical equipment having more instantaneous antibacterial activity.

Figure 3:
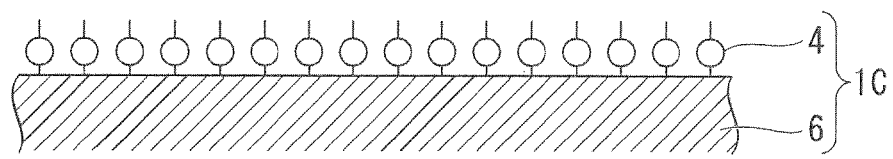
FIG. 3 is a schematic diagram showing the third embodiment of an antibacterial medical equipment of the present invention.

FIG. 3 is a schematic diagram showing the third embodiment of an antibacterial medical equipment of the present invention. The antibacterial medical equipment 10 of the present embodiment has a structure in which inositol phosphate 4 is bonded directly to a surface of a medical equipment 6 which is made of a Ca compound or contains a Ca compound.

The antibacterial medical equipment 10 of the present embodiment can be simply produced by optionally polishing or washing the surface of a medical equipment 6 and immersing the medical equipment 6 in an inositol phosphate solution thereby bonding inositol phosphate to Ca on the surface, followed by separation from the solution, washing and drying. It is also possible that an inositol phosphate solution is spray-coated on the surface of the medical equipment 6 instead of immersion in the inositol phosphate solution thereby bonding inositol phosphate to Ca on the surface.

Similar to the above-described antibacterial medical equipment 1A of the first embodiment, the antibacterial medical equipment 10 of the present embodiment has a structure in which inositol phosphate 4 is bonded to the surface of a medical equipment 6 which is made of a Ca compound or contains a Ca compound, and has operational advantages such as antibacterial activity which could have never been predicted by conventional knowledge with respect to inositol phosphate. Thus, it is possible to provide an antibacterial medical equipment which has practically sufficient antibacterial activity and is excellent in compatibility with living tissues, and also can maintain antibacterial activity over a long period and has high safety.

Figure 4:
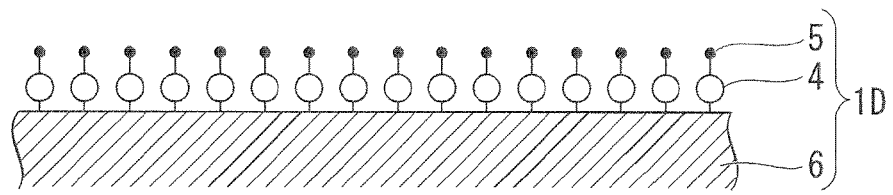
FIG. 4 is a schematic diagram showing the fourth embodiment of an antibacterial medical equipment of the present invention.

FIG. 4 is a schematic diagram showing the fourth embodiment of an antibacterial medical equipment of the present invention. The antibacterial medical equipment 1D of the present embodiment has a structure in which inositol phosphate 4 is bonded directly to a surface of a medical equipment 6 which is made of a Ca compound or contains a Ca compound, and also silver ions 5 are bonded to the inositol phosphate 4.

The antibacterial medical equipment 1D of the present embodiment can be easily produced by immersing the above-described antibacterial medical equipment 1C of the third embodiment in an Ag ion-containing solution such as an aqueous $AgNO_3$ solution, followed by taking out, washing and drying, or spray-coating the solution, followed by washing and drying. There is no particular limitation on the amount of silver ions 5 bonded, and a proper amount of silver ions 5 may be bonded according to the kind of the antibacterial medical equipment 1D and purposes. The amount of silver ions 5 bonded can be appropriately adjusted by the concentration of silver ions used for immersion and the immersion time.

Since the antibacterial medical equipment 1D of the present embodiment has a structure in which silver ions 5 are bonded to the inositol phosphate 4 in the above-described antibacterial medical equipment 1C of the third embodiment, it is possible to provide an antibacterial medical equipment having more instantaneous antibacterial activity.

EXAMPLES

The effects of the present invention will be proved by way of Examples. The following Examples of the present invention are provided merely for illustrative purposes of the present invention and the present invention is not limited by the description of Examples.

(1) Coating of Titanium Substrate with HAp (1-1) Preparation of Reagent

Preparation of Simulated Body Fluid (Hereinafter Referred to as SBF)

SBF is a solution in which the concentration of inorganic ions remaining after removing organic matter such as human cells and proteins from blood plasma in human blood is made nearly identical to that of blood plasma. The ion concentration of SBF and blood plasma is shown in Table 1.

TABLE 1

| | Ion concentration/mM | | |
|---|---|---|---|
| Ions | SBF (1.5) | SBF (1.0) | Blood plasma |
| $Na^+$ | 213.3 | 142.0 | 142.0 |
| $K^+$ | 9.1 | 5.0 | 5.0 |
| $Mg^{2+}$ | 2.3 | 1.5 | 1.5 |
| $Ca^{2+}$ | 4.0 | 2.5 | 2.5 |
| $Cl^-$ | 224.9 | 147.8 | 103.0 |
| $HCO_3^-$ | 6.3 | 4.2 | 27.0 |
| $HPO_4^{2-}$ | 1.38 | 1.0 | 1.0 |
| $SO_4^{2-}$ | 0.76 | 0.5 | 0.5 |

In Table 1, SBF (1.5) means that the amount of all solutes of a standard concentration of SBF (SBF (1.0)) was increased by 1.5 times.

Regarding SBF, using reagents described in Table 2, each reagent was added in the amount described in the table to make the entire amount to 1 $dm^3$ (36.5° C., pH 7.40). In the following Examples, SBF (1.5) was used as SBF.

TABLE 2

| Reagents | SBF (1.5) | SBF (1.0) |
|---|---|---|
| Sodium chloride NaCl | 12.053 g | 8.035 g |
| Sodium hydrogen carbonate $NaHCO_3$ | 0.532 g | 0.355 g |
| Potassium chloride KCl | 0.339 g | 0.225 g |
| Dipotassium hydrogen phosphate $K_2HPO_4$ | 0.315 g | 0.209 g |
| Magnesium chloride hexahydrate $MgCl_2 \cdot 6H_2O$ | 0.468 g | 0.311 g |
| Calcium chloride $CaCl_2$ | 0.438 g | 0.292 g |
| Sodium sulfate $Na_2SO_4$ | 0.109 g | 0.072 g |
| Hydrochloric acid (1mol/$dm^3$) | 58.5 $cm^3$ | 39.0 $cm^3$ |
| Tris(hydroxymethyl)aminomethane | 9.177 g | 6.118 g |

Preparation of Surface Treating Solution

A surface treating solution was prepared by adding urea to SEE.

Urea was added to SBF so as to adjust the concentration of urea to 2.0 mol/$dm^3$. When titanium substrate was immersed in the surface treating solution, a 1.0 mass % urease solution prepared by dissolving urease as a hydrolase of urea in pure water was added.

These two kinds of solutions were prepared.

(1-2) Preparation of Titanium Substrate

Figure 5:
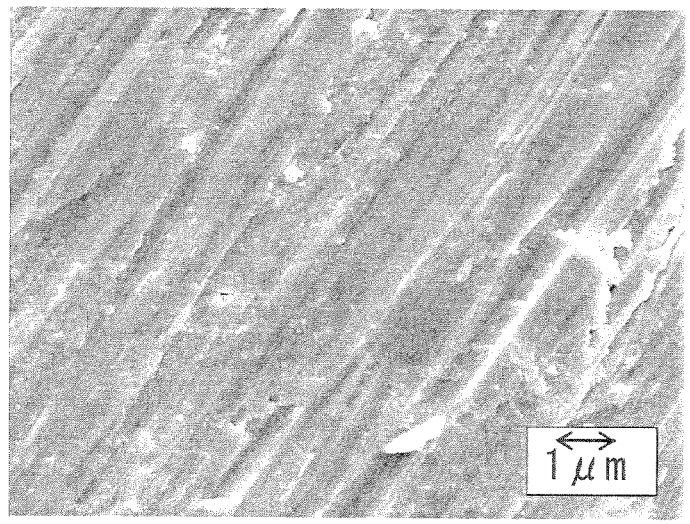
Figure 5:
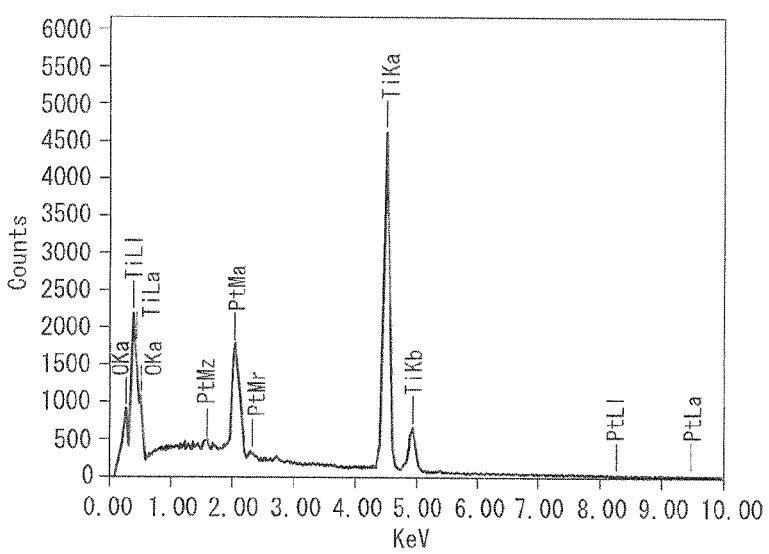
Figure 5:
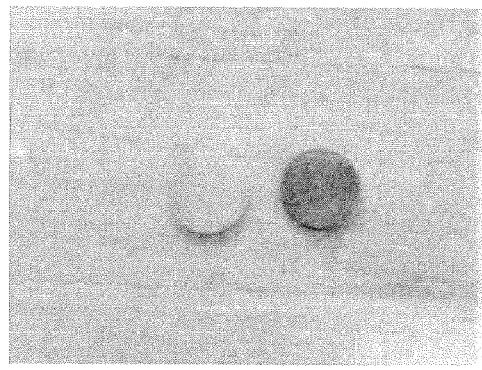

Using a polishing machine, a surface of titanium substrate was polished with a #240 abrasive paper. Then, titanium substrate was ultrasonic-washed in turn with pure water, ethanol and acetone twice for 5 minutes each, followed by air drying. FIG. 5(*a*) is an enlarged image of a surface of titanium substrate thus prepared, FIG. 5(*b*) is a graph showing measurement results of elements contained, and FIG. 5(*c*) is an appearance of titanium substrate subjected to a polishing treatment (left) and an appearance of untreated titanium substrate (right).

(1-3) Experiment Procedure

Figure 6:
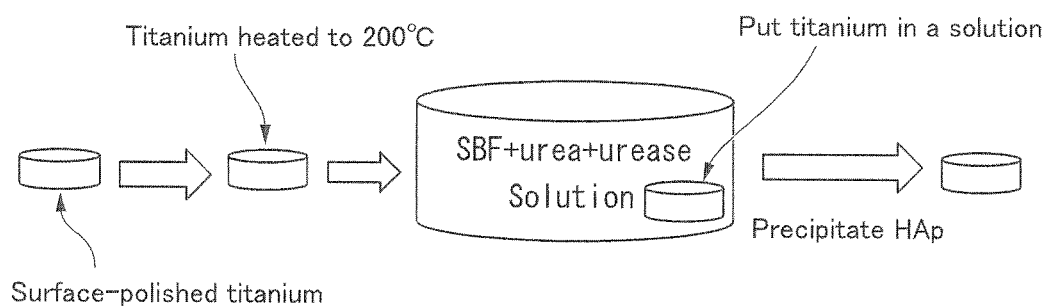
FIG. 6 is a flow chart for explaining an experiment procedure in Examples.

An experiment procedure is shown in FIG. 6. Titanium substrate subjected to surface polishing, washing and drying as described above was heated to 200° C. in air, immersed in SBF containing urea and urease, and then allowed to stand in an incubator at 50° C. for several days thereby precipitating HAp.

Solutions used in HAp coating are shown in Table 3.

New SBF was replaced on the 2nd day, 4th day and 6th day.

On the seventh day, the solution was completely drained off, followed by washing with pure water and further air drying.

TABLE 3

|  | SBF | Urease solution |
|---|---|---|
| 1st day | 5.0 cm$^3$ (containing urea) | 48.5 × 10$^{-3}$ cm$^3$ |
| 2nd day, 4th day, 6th day | 5.0 cm$^3$ (without containing urea) | 0 cm$^3$ |

Figure 7:
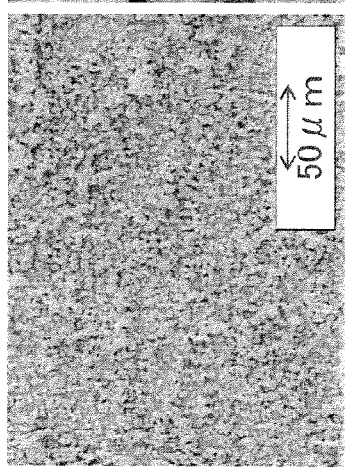
Figure 7:
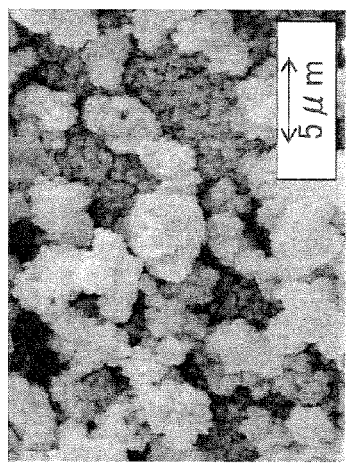
Figure 7:
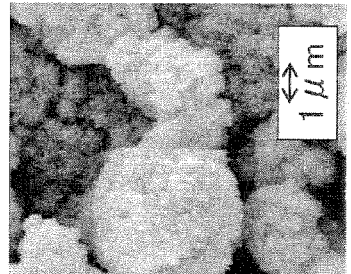
Figure 7:
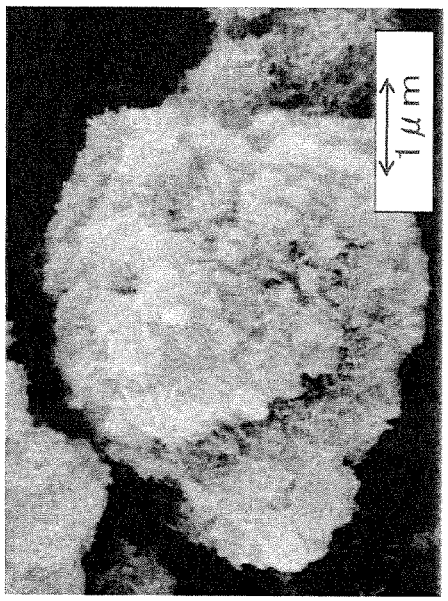
Figure 7:
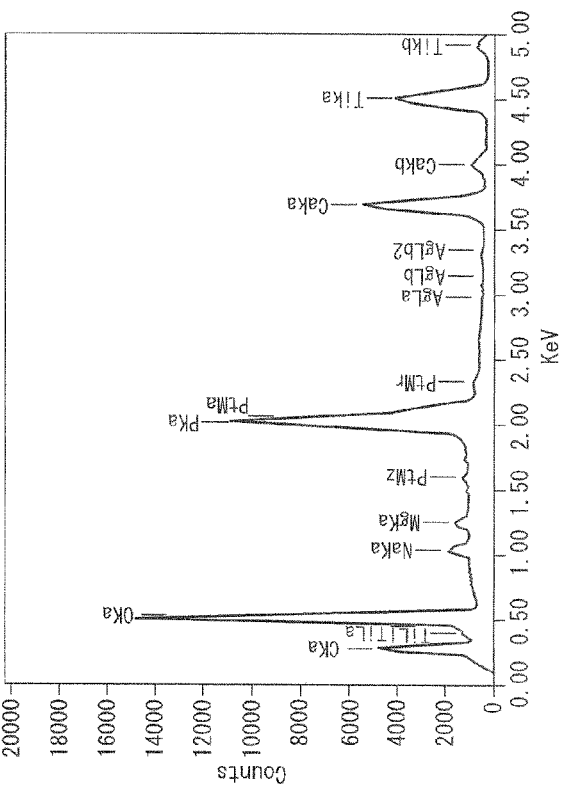

A HAp-coated titanium substrate was obtained by the above procedure. FIG. 7(a) is a SEM (scanning electron microscope) image of a surface of HAp-coated titanium substrate (magnified 500 times), FIG. 7(b) is an image magnified 5,000 times, FIG. 7(c) is an image magnified 10,000 times, FIG. 7(d) is an image magnified 20,000 times, and FIG. 7(e) is a graph showing measurement results by EDX (energy-dispersive X-ray microanalysis) of elements on the surface of HAp-coated titanium substrate. As is apparent from these results, a coating of HAp was formed on a surface of the resultant HAp-coated titanium substrate.

(2) Immobilization of Silver Ions to HAp-Coated Titanium Substrate (2-1) Preparation of Reagent Inositol Phosphate An inositol phosphate aqueous solution was used for immobilization of silver ions. In the present Example, IP$_6$ was used as inositol phosphate. IP$_6$ is a compound in which all six hydroxyl groups of inositol are esterified with phosphoric acid and is a biogenic related compound having a high cheleting effect. It has been found that inositol phosphate has higher effect of metal cheletes than that of ethylenediaminetetraacetic acid (EDTA) and also has a metal corrosion prevention effect, metal removal effect and antioxidative effect.

It is considered that, by bringing an aqueous solution of inositol phosphate into contact with HAp layer, calcium ions in HAp are bonded to inositol phosphate and also the bonded inositol phosphate chelates silver ions, and thus silver ions are immobilized to a HAp layer via inositol phosphate.

In the present Example, an aqueous 1,000 ppm solution of IP$_6$ was prepared by diluting 50% IP$_6$ solution. Using the resultant solution as an undiluted solution, four kinds of aqueous solutions were prepared by further diluting the undiluted solution.

Silver Ions

In the present Example, an aqueous AgNO$_3$ solution was used as a silver ion source.

A commercially available AgNO$_3$ (1.71 g) was dissolved in pure water to make 100 mL of a solution. Using the resultant solution as an undiluted solution, six kinds of aqueous solutions (0.00005 mol/dm$^3$, 0.0001 mol/dm$^3$, 0.0005 mol/dm$^3$, 0.001 mol/dm$^3$, 0.005 mol/dm$^3$ and 0.01 mol/dm$^3$) were prepared by further diluting the undiluted solution. AgNO$_3$ has higher solubility in pure water than that of the other silver compound. In pure water, silver ions exist as Ag$^+$.

(2-2) Experiment Method

Figure 8:
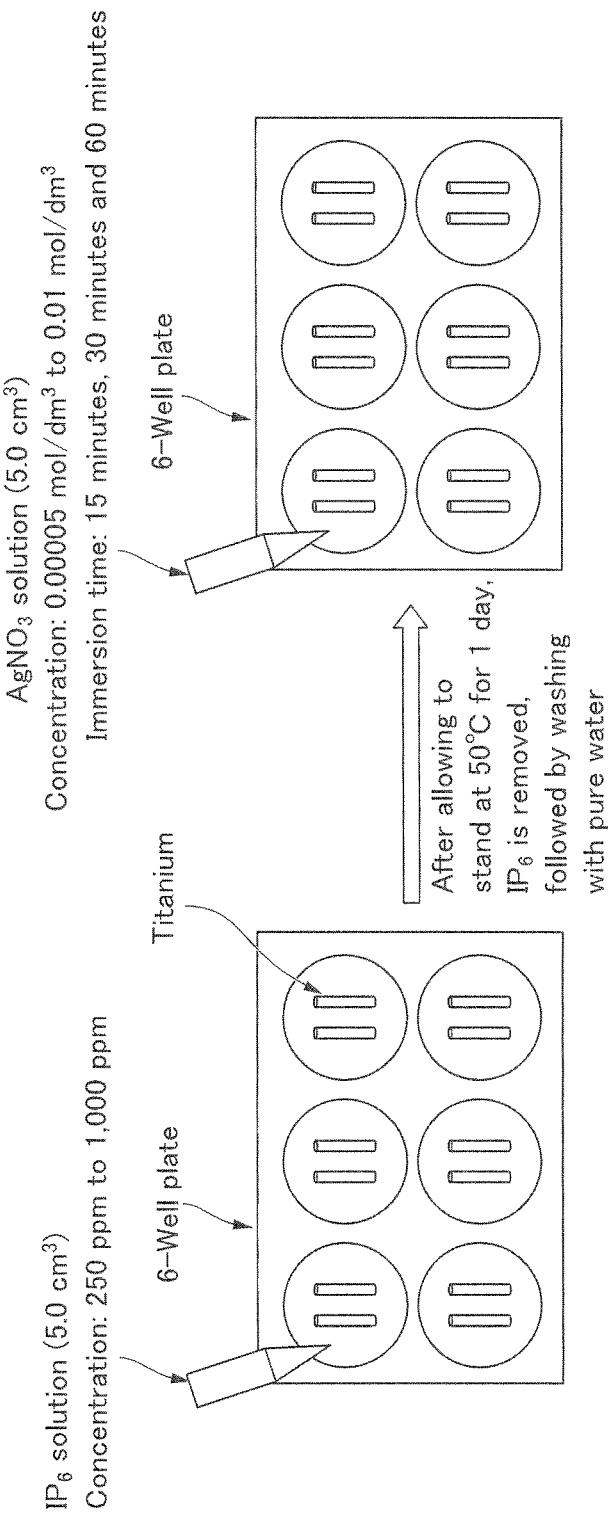
FIG. 8 is a flow chart showing a procedure for immobilization of inositol phosphate and silver ions to a surface of HAp-coated titanium in Examples.

FIG. 8 is a flow chart showing a procedure for immobilization of inositol phosphate and silver ions to the surface of HAp-coated titanium.

In the present experiment, first, the HAp-coated titanium was set in a 6-well plate and 5.0 cm$^3$ of each of IP$_6$ solutions (concentration: 250 ppm, 500 ppm, 750 ppm and 1,000 ppm) was injected into the plate and then the plate was allowed to stand at 50° C. for 1 day, and thus IP$_6$ was bonded to the surface of HAp-coated titanium.

Thereafter, the IP$_6$ solution was removed from the plate and the inside of the plate was washed several times with pure water.

Subsequently, 5.0 cm$^3$ of each of aqueous AgNO$_3$ solutions with the concentration adjusted within a range from 0.00005 to 0.01 mol/dm$^3$ was injected into the plate. After immersion for 15 minutes, 30 minutes and 60 minutes (immersion time), the titanium was taken out, sufficiently washed with pure water and then air-dried to obtain samples in which silver ions are immobilized to the HAp-coated titanium.

In the present Example, the following tests (1) to (3) were conducted with respect to immobilization of silver ions.

(1) Influence of Concentration of Inositol Phosphate

Figure 9:
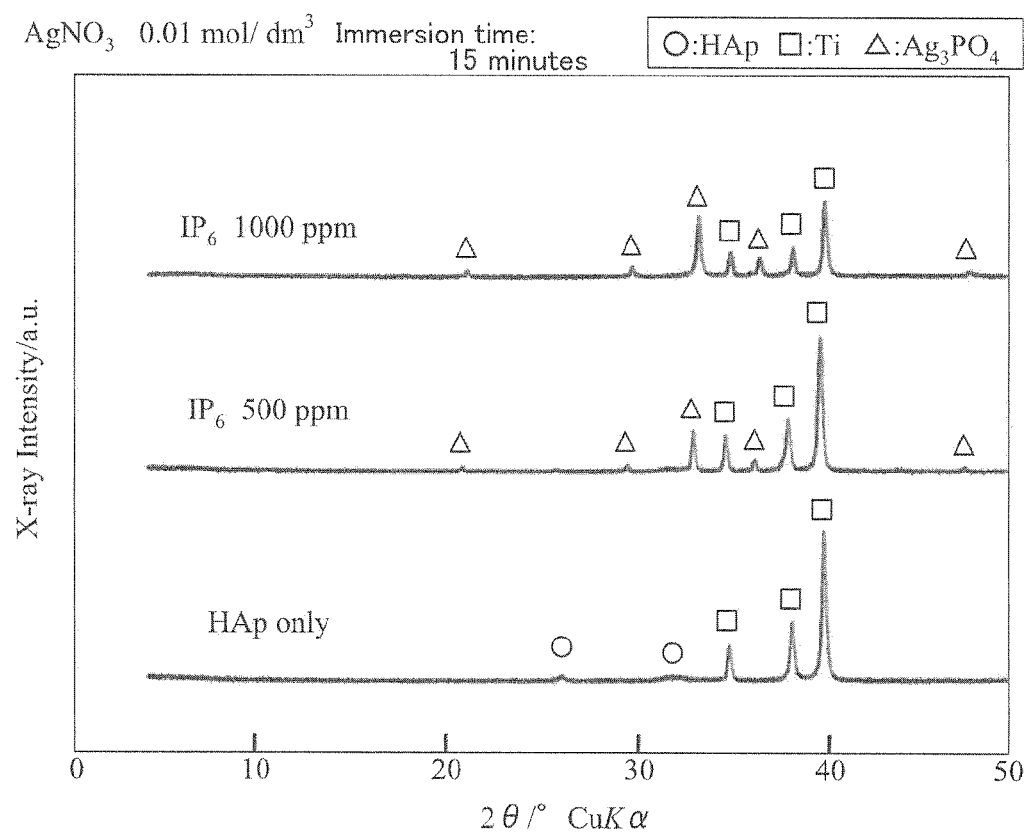
FIG. 9 is a graph showing identification results of a crystal phase of a surface of each sample obtained by an experiment in which the concentration of inositol phosphate is varied.

FIG. 9 is a graph showing X-ray diffraction results of a surface of each sample obtained by varying the concentration of inositol phosphate (IP$_6$). As is apparent from FIG. 9, in samples using inositol phosphate, existence of silver (Ag$_3$PO$_4$) on the surface can be confirmed and silver was immobilized onto the surface of each sample via inositol phosphate. In contrast, in samples made of only HAp, silver was not observed.

Figure 10:
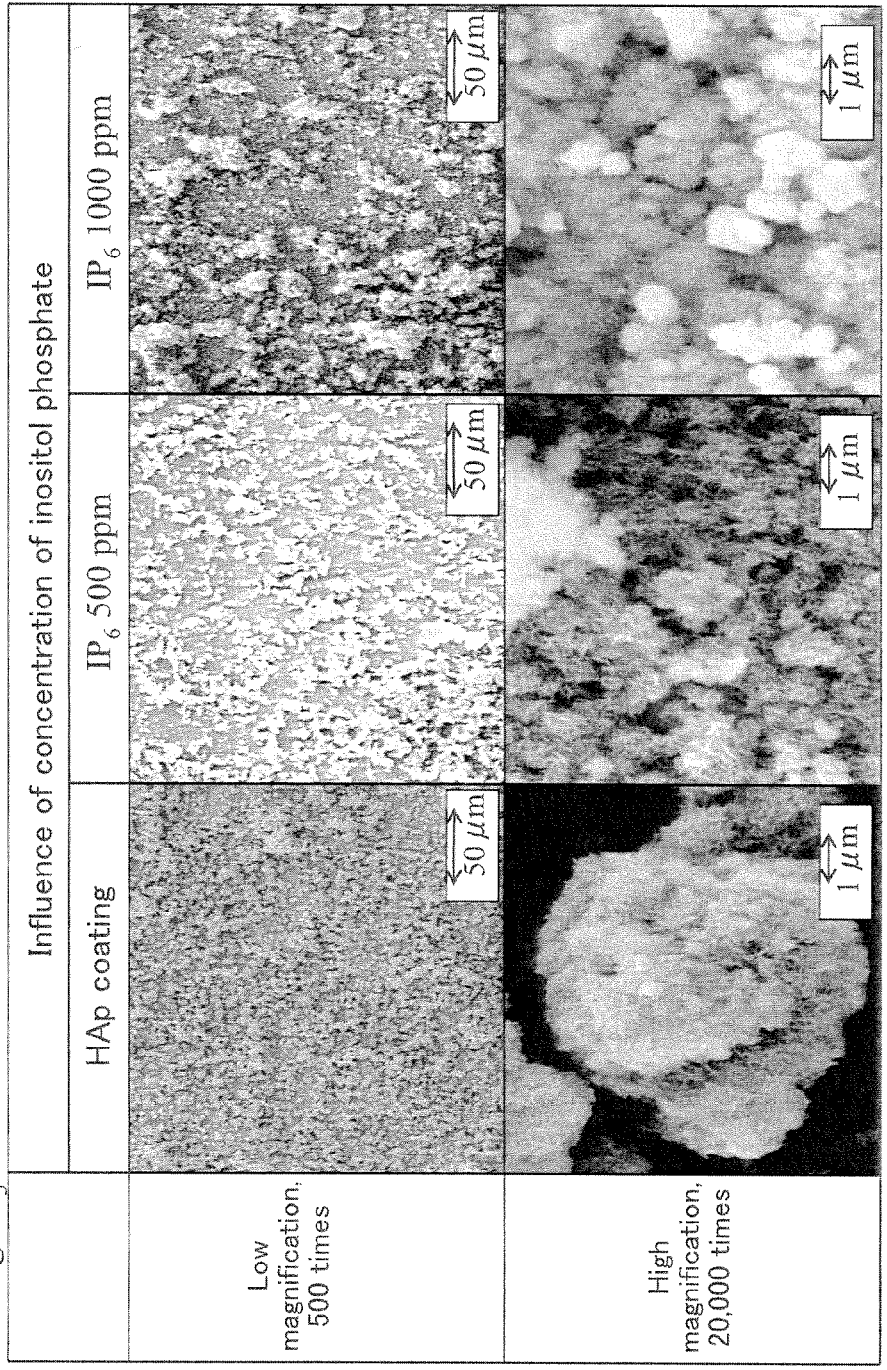
FIG. 10 is a SEM image of a surface of each sample obtained by an experiment in which the concentration of inositol phosphate is varied.

FIG. 10 is a SEM image of a surface of each sample produced by varying the concentration of inositol phosphate (IP$_6$).

Figure 11:
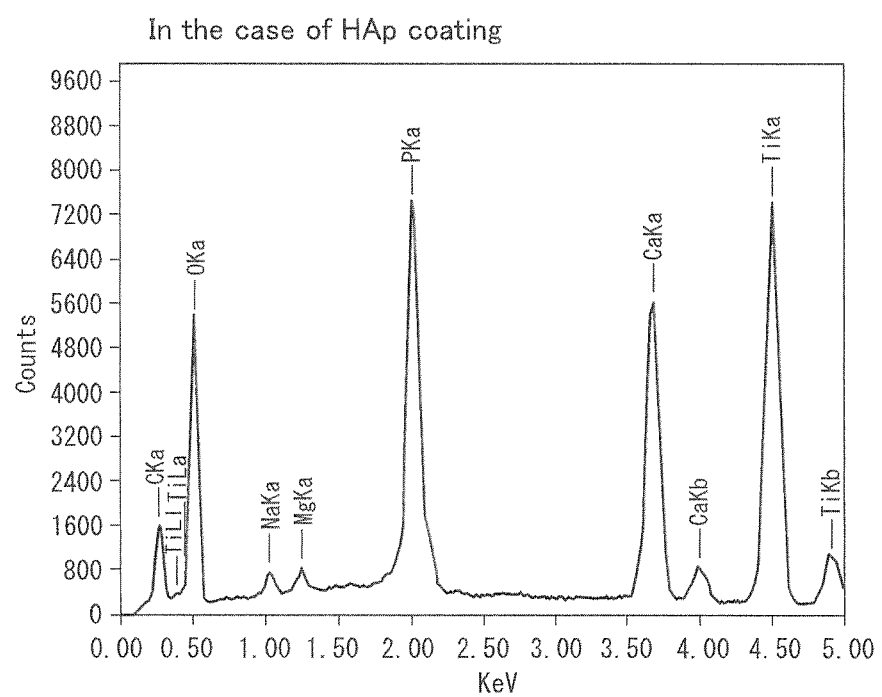
FIG. 11 shows an EDX spectrum of HAp-coated titanium.

FIG. 11 is a graph showing measurement results by EDX of elements contained on a surface coated with HAp of each sample. In the samples, a peak assigned to Ag was not observed.

Figure 12:
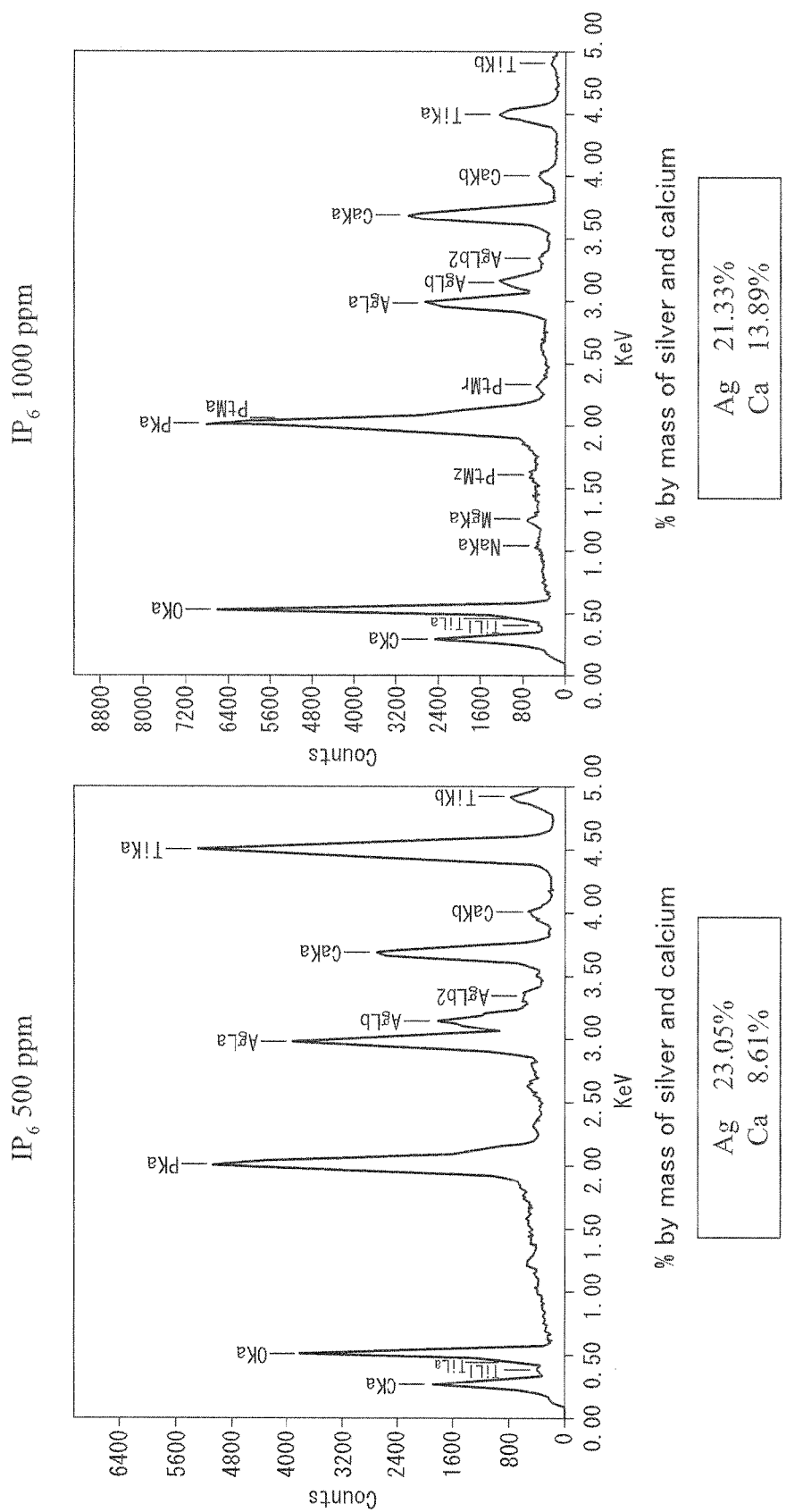
FIG. 12 shows EDX spectra of each sample obtained in an experiment in which the concentration of inositol phosphate is varied.

FIG. 12 is a graph showing measurement results by EDX of elements contained in a surface of each sample obtained by varying the concentration of inositol phosphate (IP$_6$).

Figure 13:
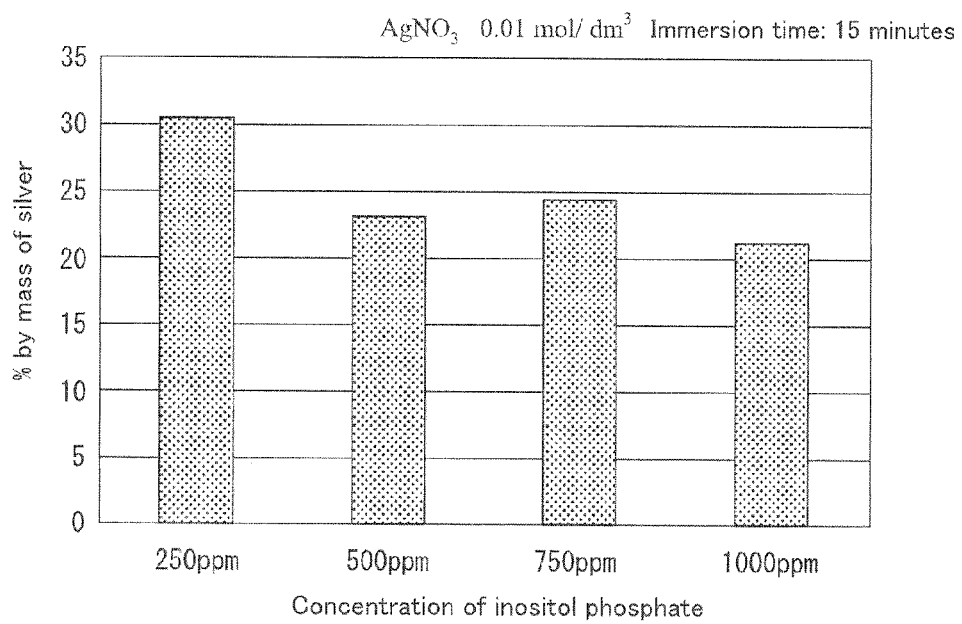
FIG. 13 is a graph showing the content of silver on a surface of each sample obtained in an experiment in which the concentration of inositol phosphate is varied.

FIG. 13 is a graph showing a relationship between the concentration of inositol phosphate (IP$_6$) and the content of silver on a surface of each sample.

Figure 14:
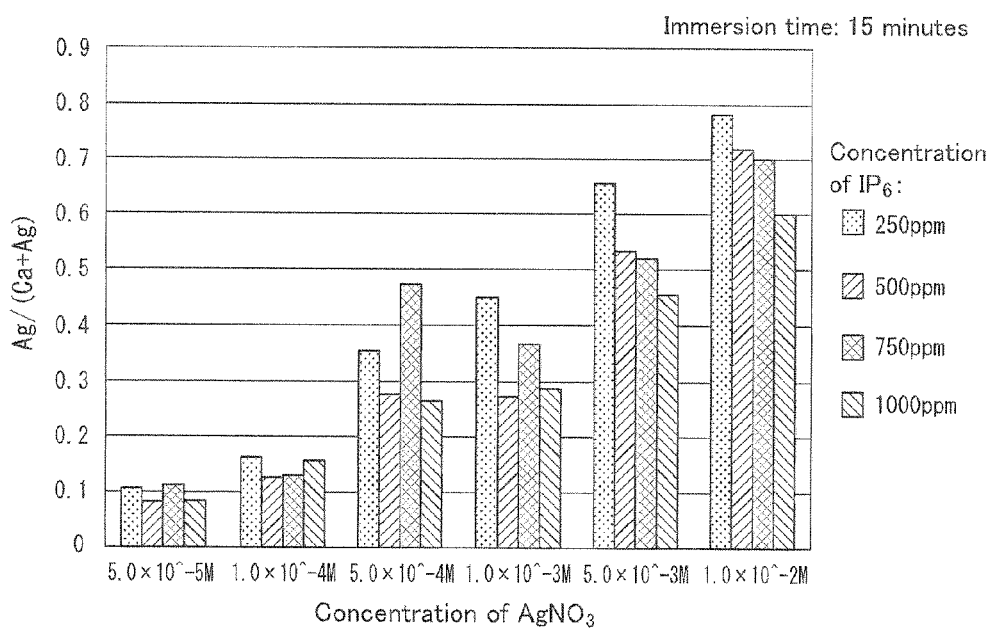
FIG. 14 is a graph showing a relationship among the concentration of inositol phosphate, the concentration of silver nitrate (hereinafter referred to as $AgNO_3$) in aqueous solution and the value of Ag/(Ca+Ag) in an experiment in which the concentration of inositol phosphate is varied.

FIG. 14 is a graph showing a relationship between the concentration of AgNO$_3$ and the ratio of Ag/(Ca+Ag) of a surface of each sample.

Summarizing the results of the test (1), it could be confirmed that silver was contained in any case where the concentration of inositol phosphate is varied within a range from 250 ppm to 1,000 ppm (four kinds). Even when the concentration of inositol phosphate varied, % by mass of silver was from 20% to 30% and thus a large variation was not recognized. As is apparent from the results shown in FIG. 14, when the concentration of AgNO$_3$ becomes less than 0.005 ppm, dependency on the concentration of inositol phosphate becomes unstable.

The following tests were conducted at the concentration of inositol phosphate of 1,000 ppm.

(2) Influence of Variation of the Concentration of AgNO$_3$ in Aqueous Solution

Figure 15:
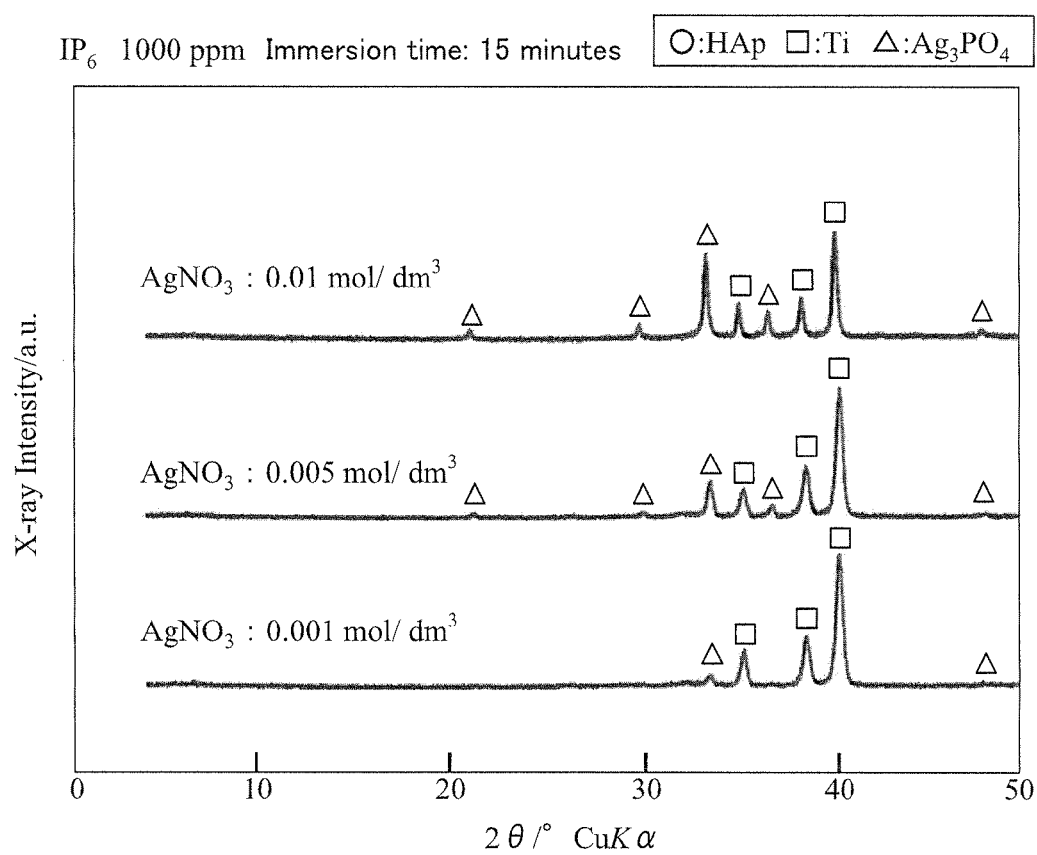
FIG. 15 is a graph showing X-ray diffraction results of a surface of each sample obtained by an experiment in which the concentration of $AgNO_3$ in aqueous solution is varied.

FIG. 15 is a graph showing X-ray diffraction results of a surface of each sample made by varying the concentration of AgNO$_3$.

Figure 16:
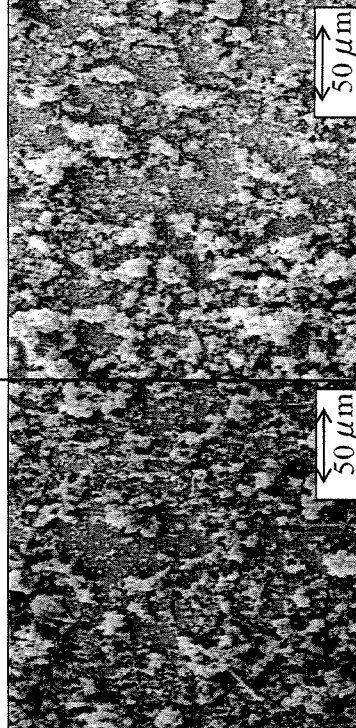
FIG. 16 is SEM image of a surface of each sample obtained in an experiment in which the concentration of $AgNO_3$ in aqueous solution is varied.

FIG. 16 is SEM image of a surface of each sample made by varying the concentration of AgNO$_3$.

Figure 17:
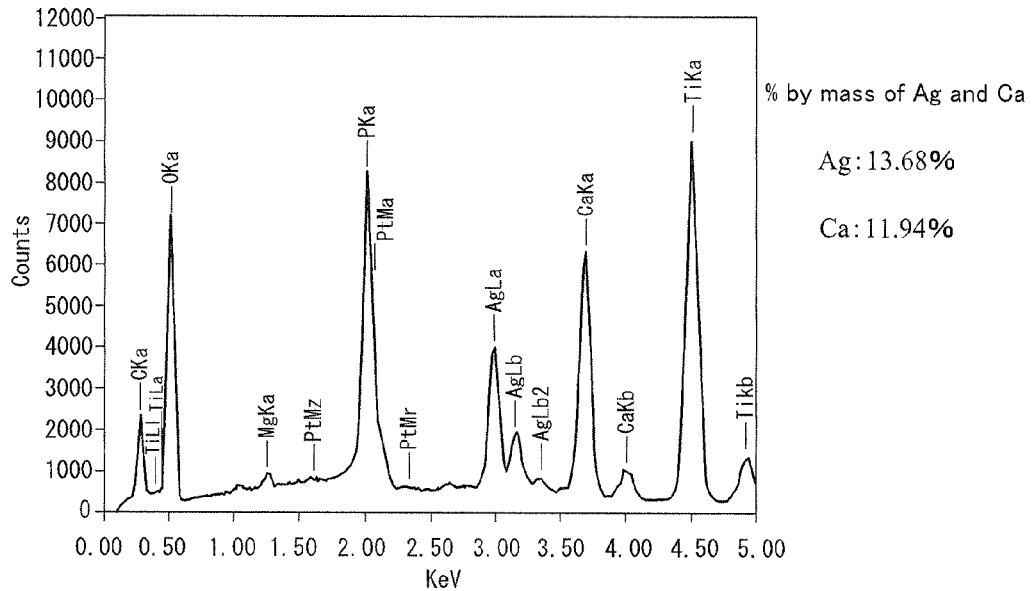
FIG. 17 shows an EDX spectrum of the sample made under the conditions of $IP_6$ concentration of 1,000 ppm, $AgNO_3$ concentration of 0.001 mol/dm$^3$ and the immersion time of 15 minutes.

FIG. 17 is a graph showing measurement results by EDX of elements contained in a surface of each sample made under the conditions of the IP$_6$ concentration of 1,000 ppm, the AgNO$_3$ concentration of 0.001 mol/dm$^3$ and the immersion time of 15 minutes.

Figure 18:
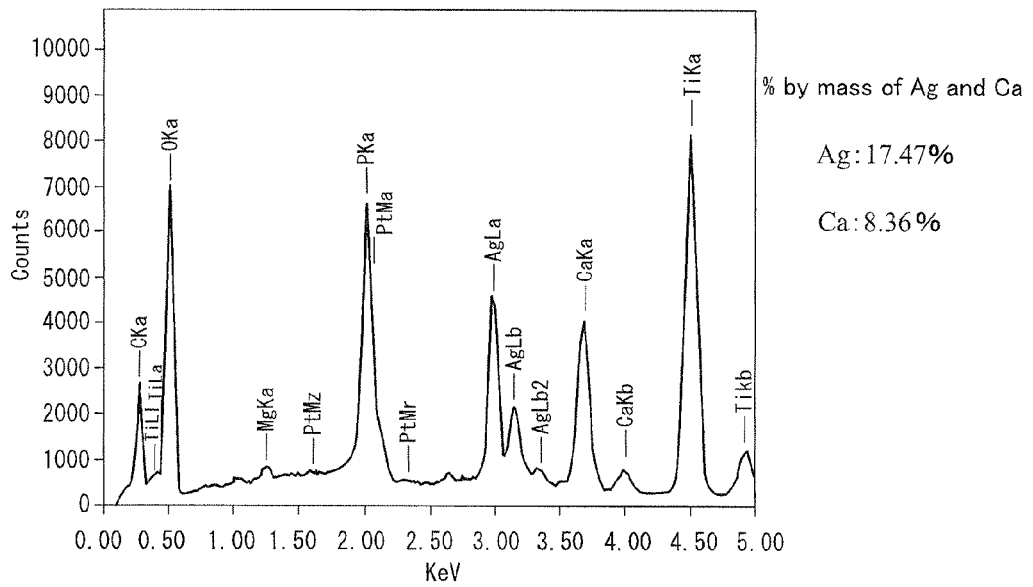
FIG. 18 shows an EDX spectrum of the sample made under the conditions of $IP_6$ concentration of 1,000 ppm, $AgNO_3$ concentration of 0.005 mol/dm$^3$ and the immersion time of 15 minutes.

FIG. 18 is a graph showing measurement results by EDX of elements contained in a surface of each sample made under the conditions of the IP$_6$ concentration of 1,000 ppm, the AgNO$_3$ concentration of 0.005 mol/dm$^3$ and the immersion time of 15 minutes.

Figure 19:
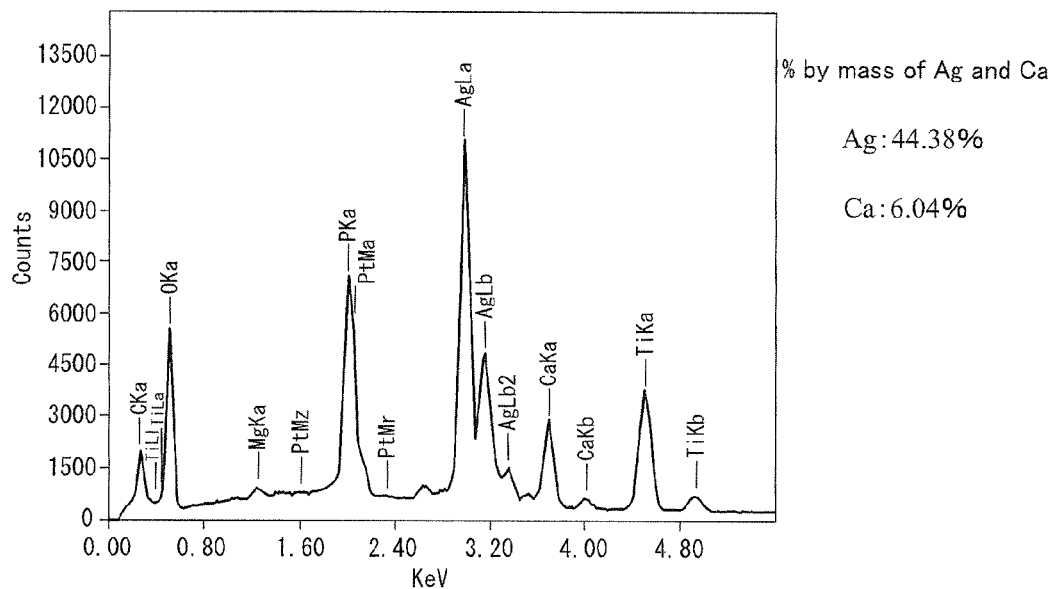
FIG. 19 shows an EDX spectrum of the sample made under the conditions of $IP_6$ concentration of 1,000 ppm, $AgNO_3$ concentration of 0.01 mol/dm$^3$ and the immersion time of 15 minutes.

FIG. 19 is a graph showing measurement results by EDX of elements contained in a surface of each sample made under the conditions of the $IP_6$ concentration of 1,000 ppm, the $AgNO_3$ concentration of 0.01 mol/dm$^3$ and the immersion time of 15 minutes.

Figure 20:
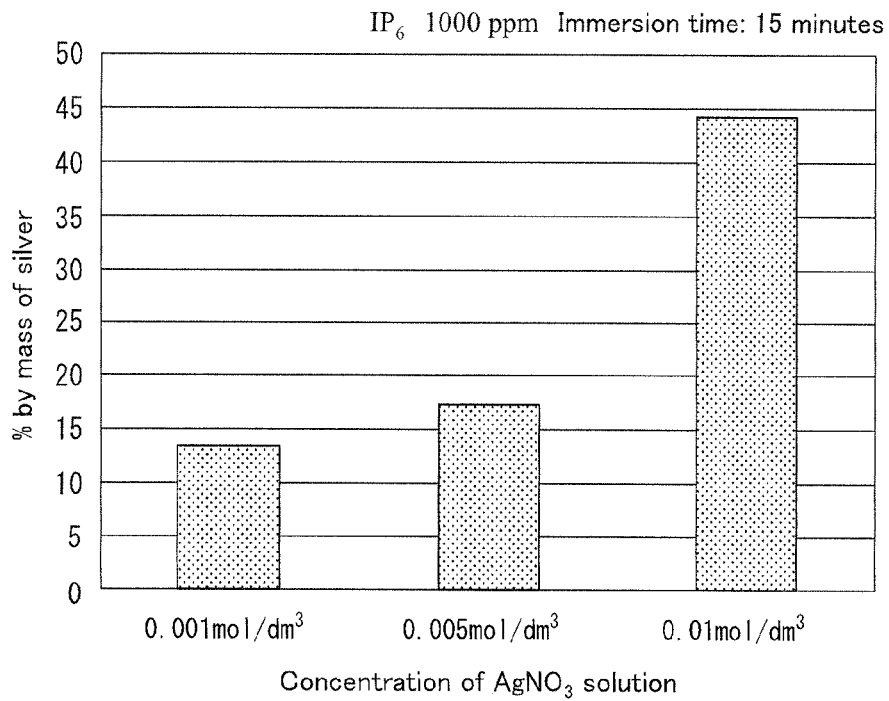
FIG. 20 is a graph showing a relationship between the concentration of $AgNO_3$ in aqueous solution and the content of silver on a surface of each sample in an experiment in which the concentration of $AgNO_3$ in aqueous solution is varied.

FIG. 20 is a graph showing a relationship between the concentration of $AgNO_3$ and the content of silver on a surface of each sample.

Figure 21:
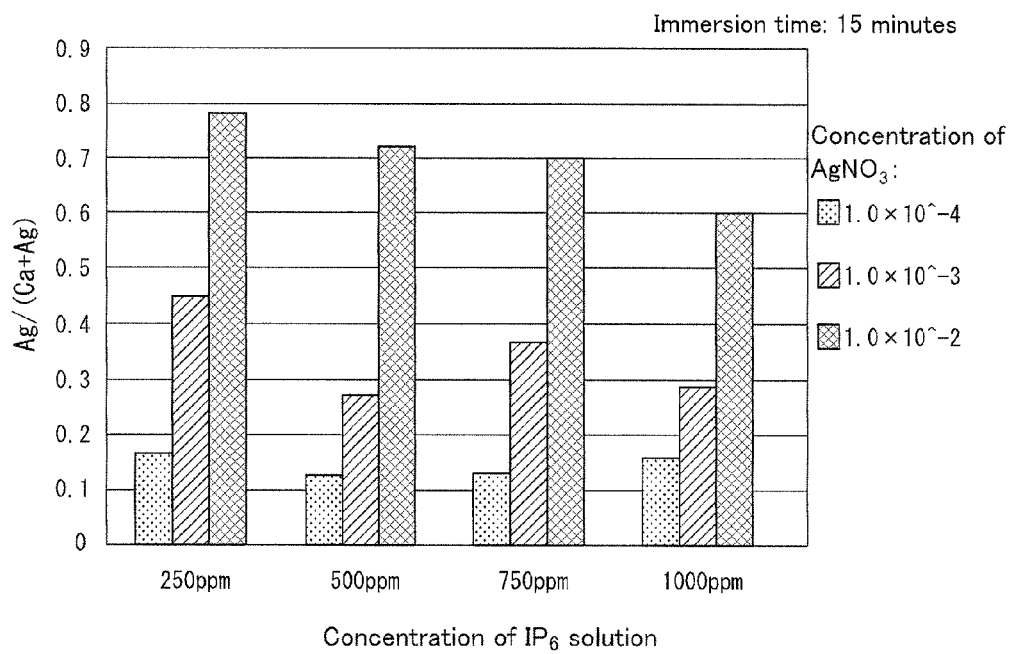
FIG. 21 is a graph showing a relationship between the concentration of $IP_6$ and the value of Ag/(Ca+Ag) in an experiment in which the concentration of $AgNO_3$ in aqueous solution is varied.

FIG. 21 is a graph showing a relationship between the concentration of $IP_6$ and the ratio of Ag/(Ca+Ag) of the surface of each sample.

Summarizing the results of the test (2), it was found that when the time of immersion in an aqueous $AgNO_3$ solution and the concentration of inositol phosphate were made to be constant, the content of silver increases as the concentration of $AgNO_3$ becomes higher. Thus, it is considered that it is possible to adjust the amount of silver ions to be added to the surface in the production of an antibacterial medical equipment by controlling the concentration of $AgNO_3$.

However, it is known that the resultant antibacterial medical equipment exhibits cytotoxicity when the amount of silver is too large. It is important to control so that a proper amount of silver can be added to the antibacterial medical equipment.

(3) Influence of Variation of Time of Immersion in $AgNO_3$ Solution

Figure 22:
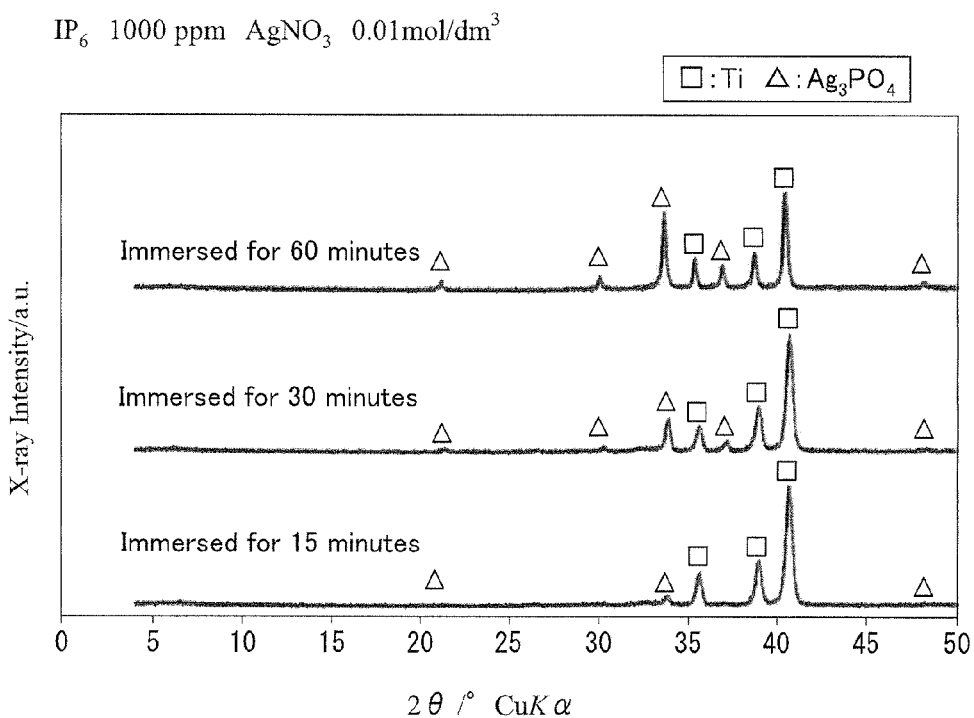
FIG. 22 is a graph showing identified X-ray diffraction results of a crystal phase of a surface of each sample obtained in an experiment in which the time of immersion in an aqueous $AgNO_3$ solution is varied.

FIG. 22 is a graph showing X-ray diffraction results of a surface of each sample made by varying the immersion time under the conditions of the $IP_6$ concentration of 1,000 ppm and the $AgNO_3$ concentration of 0.01 mol/dm$^3$.

Figure 23:
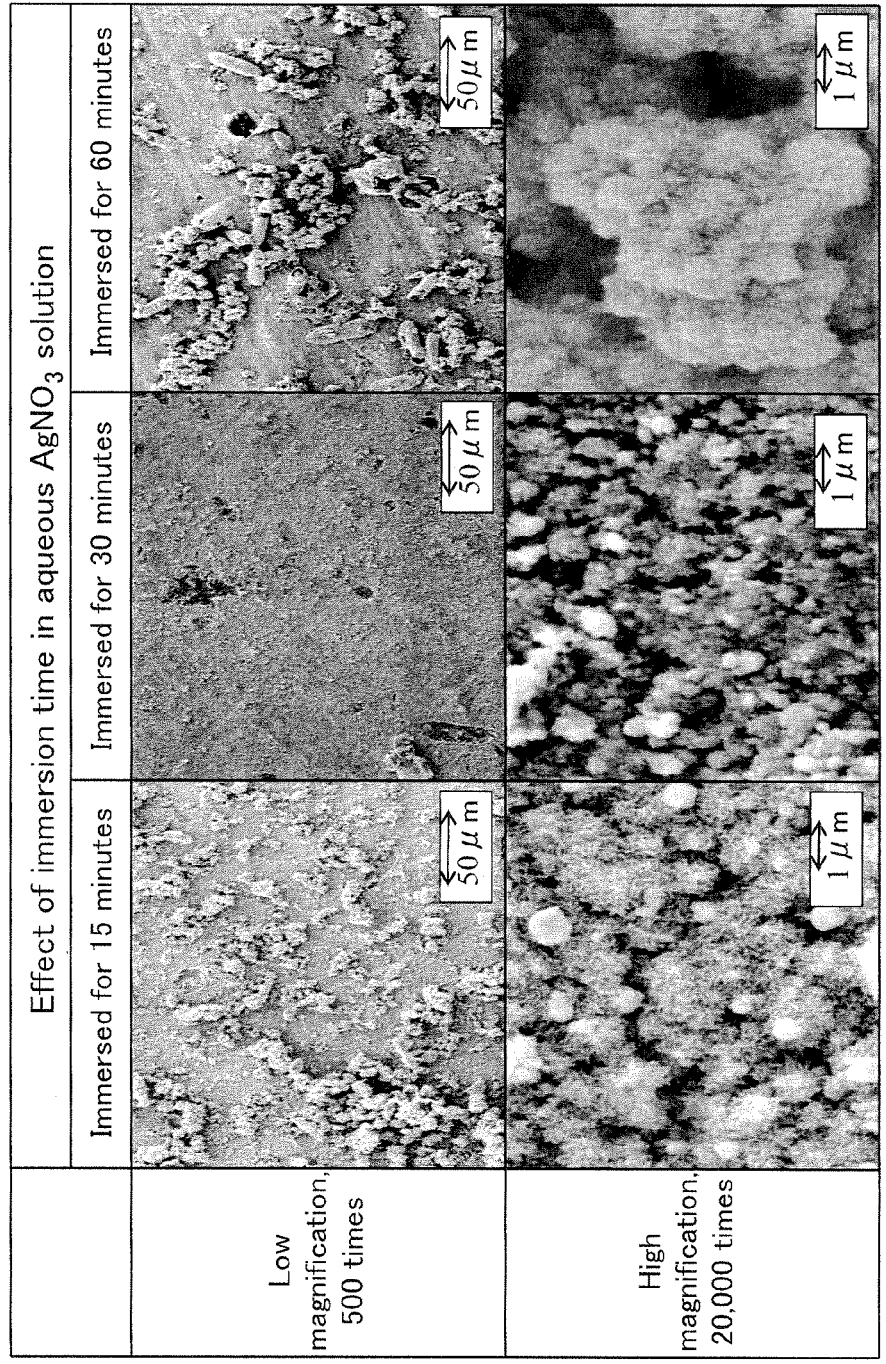
FIG. 23 is a SEM image of a surface of each sample obtained in an experiment in which the time of immersion in an aqueous $AgNO_3$ solution is varied.

FIG. 23 is a SEM image of a surface of each sample made by varying the immersion time.

Figure 24:
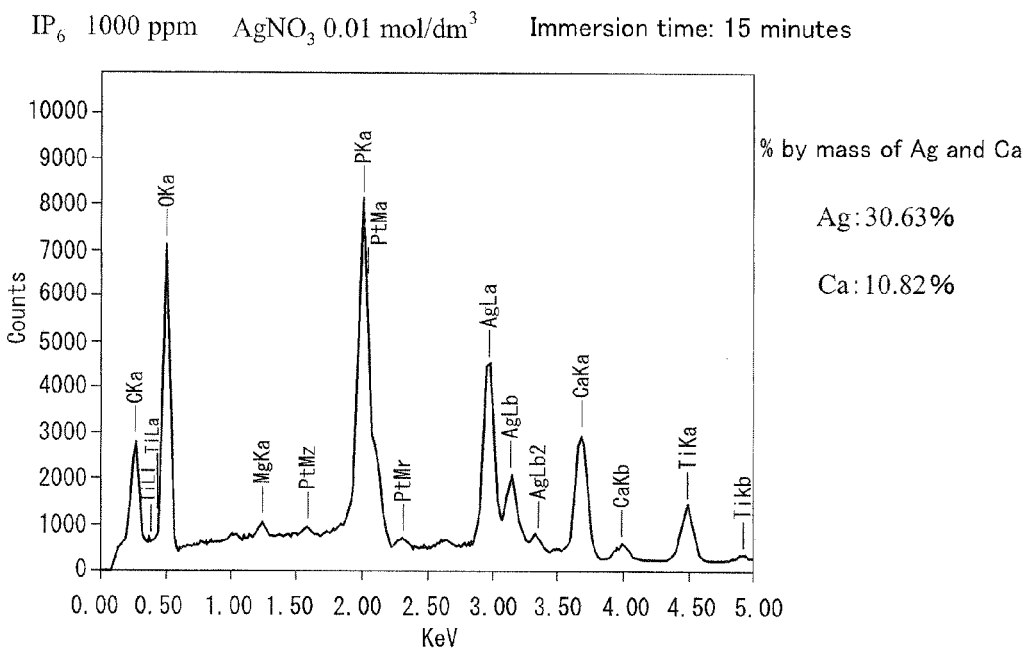
FIG. 24 shows an EDX spectrum of the sample made under the conditions of $IP_6$ concentration of 1,000 ppm, $AgNO_3$ concentration of 0.01 mol/dm$^3$ and the immersion time of 15 minutes.

FIG. 24 is a graph showing measurement results by EDX of elements contained in a surface of each sample made under the conditions of the $IP_6$ concentration of 1,000 ppm, the $AgNO_3$ concentration of 0.01 mol/dm$^3$ and the immersion time of 15 minutes.

Figure 25:
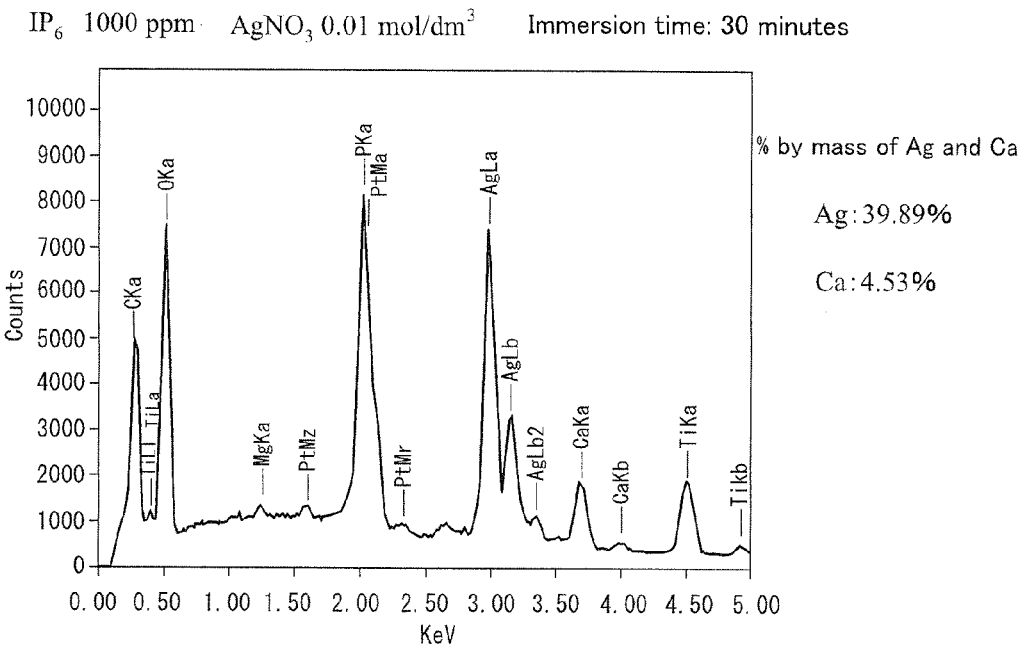
FIG. 25 shows an EDX spectrum of the sample made under the conditions of $IP_6$ concentration of 1,000 ppm, $AgNO_3$ concentration of 0.01 mol/dm$^3$ and the immersion time of 30 minutes.

FIG. 25 is a graph showing examination results of elements contained in a surface of each sample made under the conditions of the $IP_6$ concentration of 1,000 ppm, the $AgNO_3$ concentration of 0.01 mol/dm$^3$ and the immersion time of 30 minutes.

Figure 26:
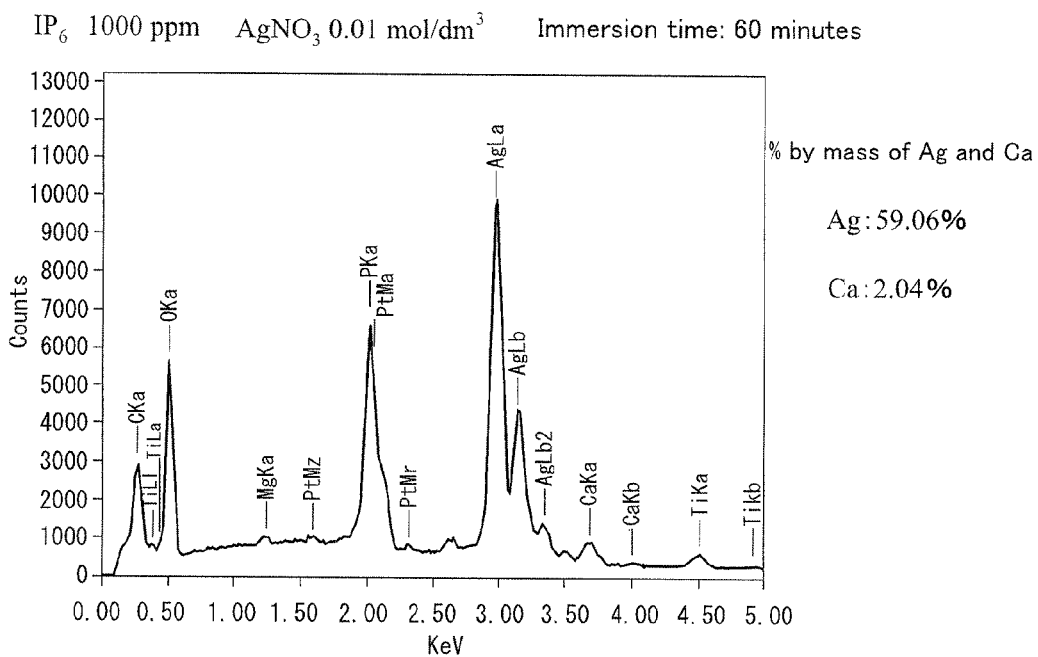
FIG. 26 shows an EDX spectra of the sample made under the conditions of $IP_6$ concentration of 1,000 ppm, $AgNO_3$ concentration of 0.01 mol/dm$^3$ and the immersion time of 60 minutes.

FIG. 26 is a graph showing examination results by EDX of elements contained in a surface of each sample made under the conditions of the $IP_6$ concentration of 1,000 ppm, the $AgNO_3$ concentration of 0.01 mol/dm$^3$ and the immersion time of 60 minutes.

Figure 27:
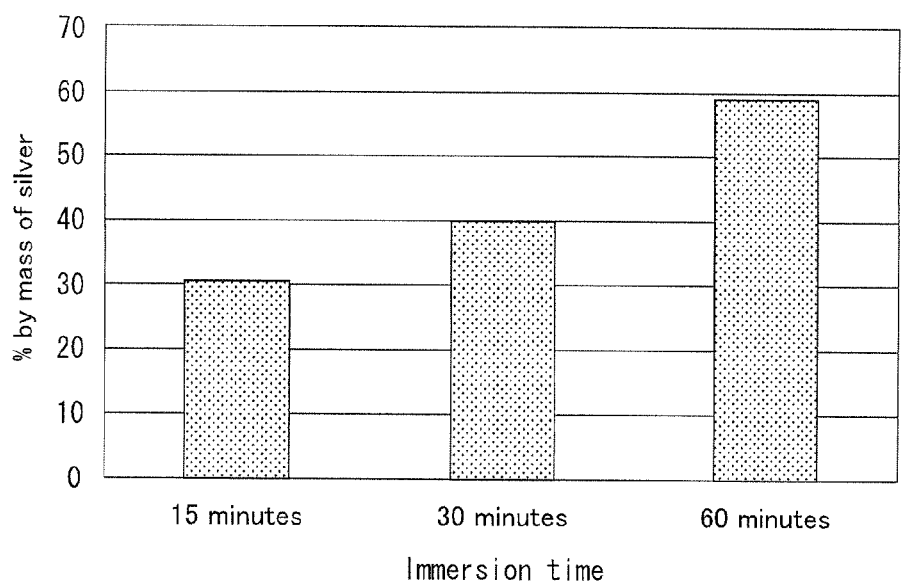
FIG. 27 is a graph showing a relationship between the immersion time and the content of silver on a surface of each sample in an experiment in which the time of immersion in an aqueous $AgNO_3$ solution is varied.

FIG. 27 is a graph showing a relationship between the immersion time in an aqueous $AgNO_3$ solution and the content of silver of a surface of each sample.

Figure 28:
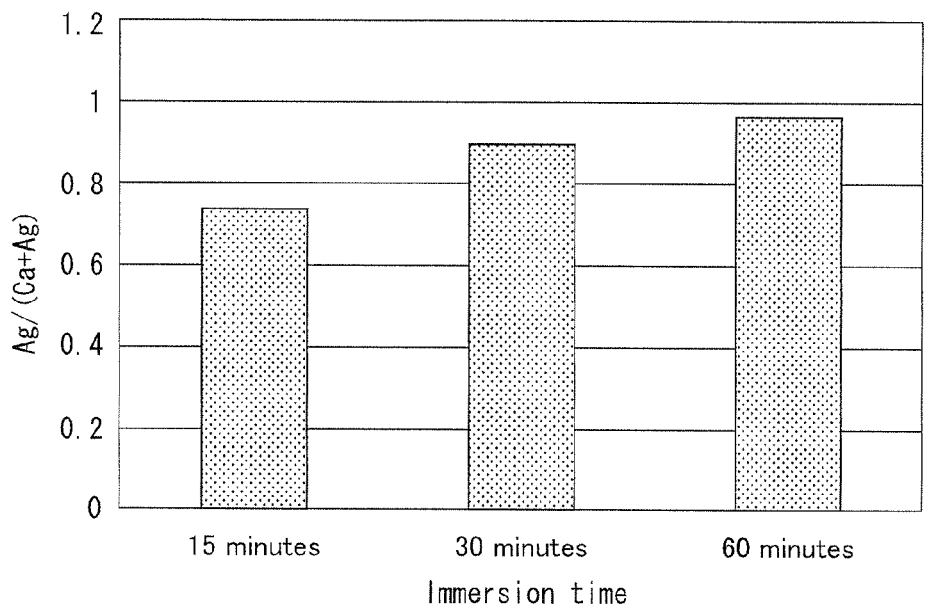
FIG. 28 is a graph showing a relationship between the immersion time and the value of Ag/(Ca+Ag).

FIG. 28 is a graph showing a relationship between immersion time in an aqueous $AgNO_3$ solution and the ratio of Ag/(Ca+Ag) of the surface of each sample.

Summarizing the results of the test (3), when the concentration of inositol phosphate and that of $AgNO_3$ were made to be constant and the immersion time was varied, the content of silver increased as the immersion times became longer. However, as is apparent from the results by EDX, when the immersion time was 60 minutes, the content of "calcium" was very low and that of silver was considerably high.

During the immersion time in the aqueous $AgNO_3$ solution, the content of silver increased, while that of calcium decreased.

The following facts have been found from a series of the above tests.

Regarding Form of Silver:

It could be confirmed that silver was contained when inositol phosphate was used. As is apparent from a graph of XRD, silver exists in the form of "silver phosphate". It could also be confirmed from the results of EDX that silver and calcium coexist. Since particles having a characteristic squamous form were observed in HAp which was precipitated from SBF in SEM observation, it is considered that an original HAp layer was converted into a mixed layer of silver phosphate and HAp in the present process.

Regarding Content of Silver:

It has been found that the content of silver can be controlled by the concentration of $AgNO_3$ and the immersion time. When immersed in the aqueous $AgNO_3$ solution for a long time, or when immersed in the solution having a high concentration, the amount of calcium decreased. It has been found that since HAp is dissolved under the acidic condition, it must be immersed in the aqueous $AgNO_3$ solution in as short a time as possible.

[Antibacterial Activity Test]

In accordance with preferred production conditions obtained from the above-described results, samples for carrying out an antibacterial activity test were produced. These samples were produced using a pure titanium implant (0.5 mm in diameter and 8 mm in length) as a material so as to transplant to the thighbone of a mouse.

(Sample No. 1)

A pure titanium implant (0.5 mm in diameter and 8 mm in length) was used without being treated (hereinafter sometimes referred to as "Ti").

(Sample No. 2)

The surface of the Ti was polished with a #240 abrasive paper, ultrasonic-washed in turn with pure water, ethanol and acetone twice for 5 minutes each, followed by air drying to obtain samples (hereinafter sometimes referred to as "Ti (acetone treatment)").

(Sample No. 3)

A pure titanium implant was subjected to polishing, washing and drying in the same manner as in the sample No. 2, heated to 200° C. in air, followed by standing to cool to obtain samples (hereinafter sometimes referred to as "Ti (heat treatment)").

(Sample No. 4)

A pure titanium implant was heated to 200° C. in air in the same manner as in the sample No. 3, immersed in a SBF solution of urea+urease as shown in FIG. 6, allowed to stand for 7 days while replacing with the fresh solution, thereby precipitating and coating HAp on a surface, washed with pure water and then air-dried to obtain samples (hereinafter sometimes referred to as "HAp-Ti").

(Sample No. 5)

After coating HAp on a surface of a pure titanium implant in the same manner as in the sample No. 4, the coated pure titanium implant was immersed in an aqueous $IP_6$ solution (temperature 50° C.) having a concentration of 1,000 ppm for 1 day, taken out, washed with pure water and then air-dried to obtain samples (hereinafter sometimes referred to as "HAp-$IP_6$-Ti").

(Sample No. 6)

A pure titanium implant was immersed in an aqueous $IP_6$ solution in the same manner as in the case of the implant sample No. 5, immersed in an aqueous $AgNO_3$ solution having a concentration of 0.001 mol/dm$^3$ for 15 minutes thereby immobilizing silver ions, washed with pure water and then air-dried to obtain samples (hereinafter sometimes referred to as "HAp-$IP_6$-Ag—Ti Ag 0.001M").

(Sample No. 7)

A pure titanium implant was immersed in an aqueous $IP_6$ solution in the same manner as in the case of the implant sample No. 5, immersed in an aqueous $AgNO_3$ solution having a concentration of 0.005 mol/dm$^3$ for 15 minutes thereby immobilizing silver ions, washed with pure water and then air-dried to obtain samples (hereinafter sometimes referred to as "HAp-IP$_6$-Ag—Ti Ag 0.005M").

(Sample No. 8)

A pure titanium implant was immersed in an aqueous IP$_6$ solution in the same manner as in the case of the implant sample No. 5, immersed in an aqueous AgNO$_3$ solution having a concentration of 0.01 mol/dm$^3$ for 15 minutes thereby immobilizing silver ions, washed with pure water and then air-dried to obtain samples (hereinafter sometimes referred to as "HAp-IP$_6$-Ag—Ti Ag 0.01M").

(1) In Vitro Petri Dish Test

Samples Nos. 1 to 8 were radially placed on luciferase-expressing *Staphylococcus aureus* in a LB agar medium in a Petri dish at 37° C. for 24 hours, and then a bacterial growth state around each implant was examined.

Figure 29:
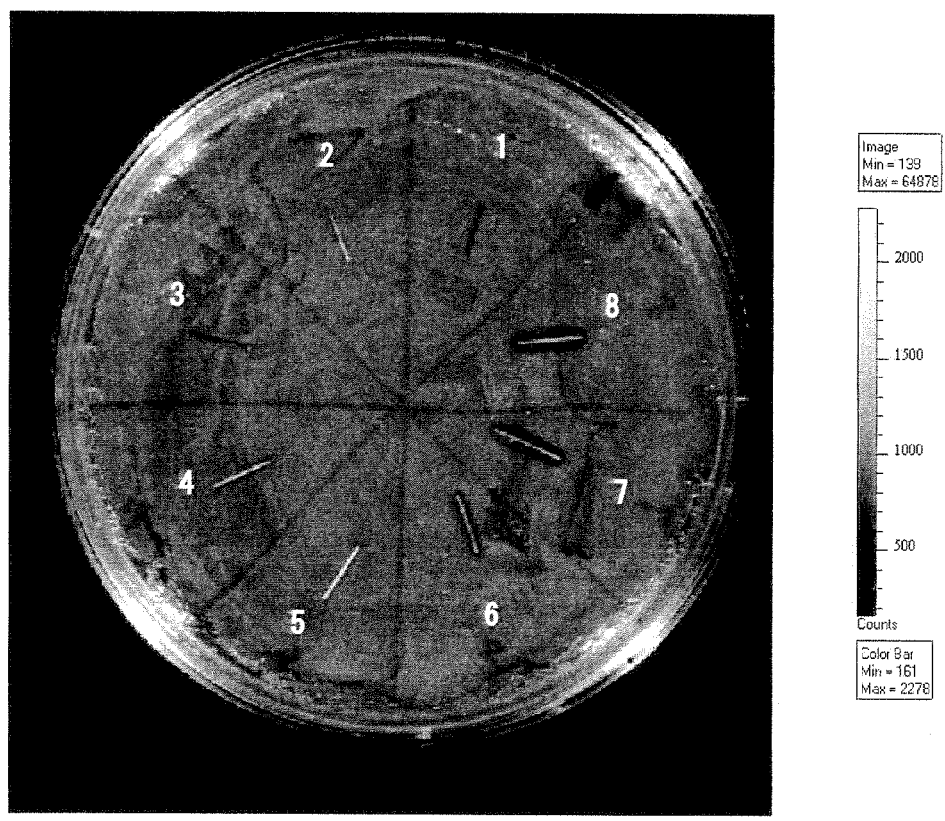
FIG. 29 is a phase-contrast image of bacteria in a Petri dish showing results of an antibacterial activity of samples No. 1 to No. 8.
Figure 31:
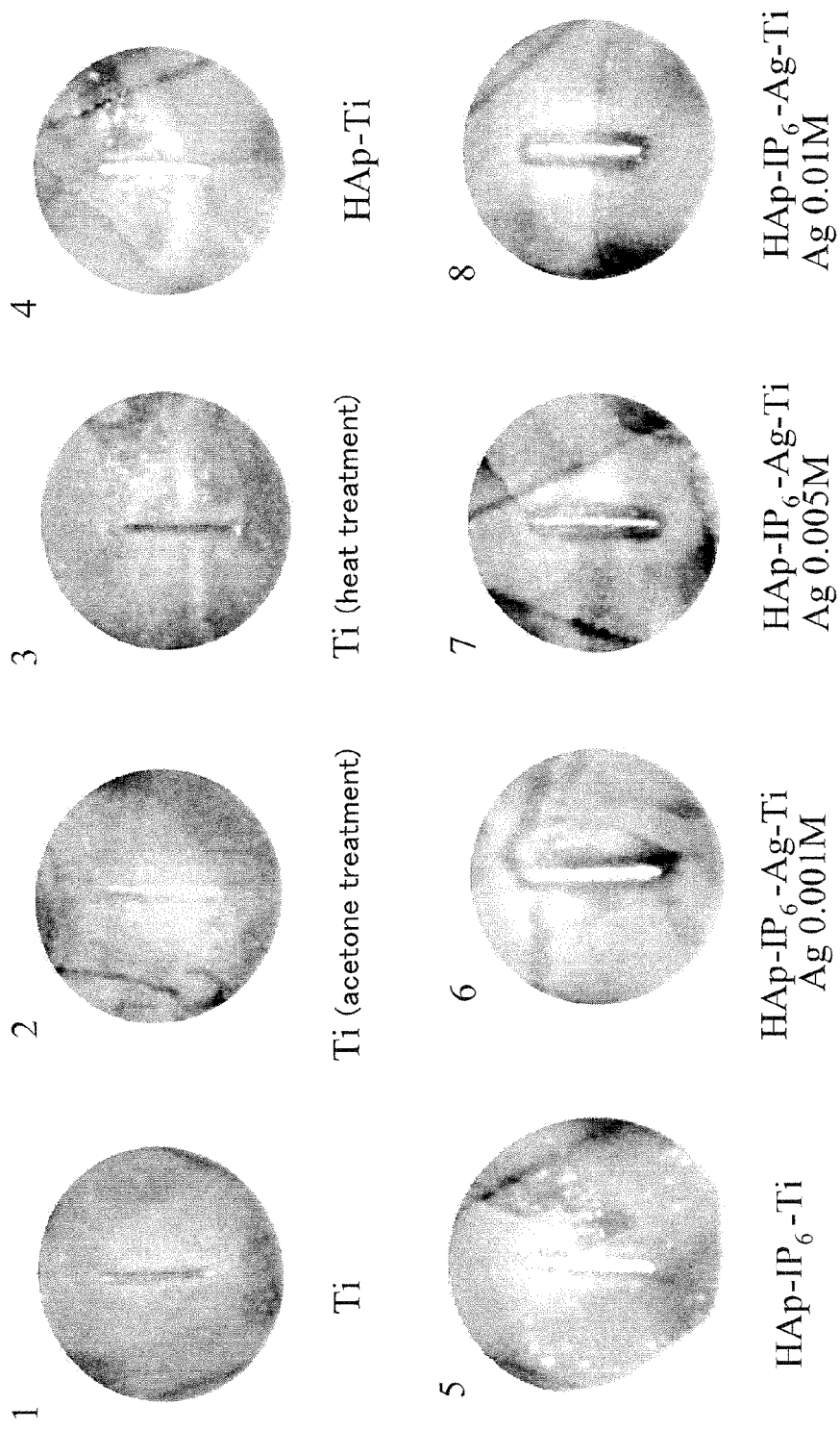
FIG. 31 shows phase-contrast images (high magnification) of bacteria in a Petri dish, indicating results of an antibacterial activity of samples No. 1 to No. 8.

FIG. 29 is a phase-contrast image of the entire Petri dish with bacteria after placement of sample Nos. 1 to 8. FIG. 31 shows phase-contrast images of bacterial growth around each of implants Nos. 1 to 8 in the Petri dish. As is apparent from these drawings, the non-growing sites (black) of bacteria were observed around implants only in samples Nos. 6 to 8 with immobilized silver ions, suggesting the strong antibacterial activity. It has also been detected that the sample No. 5, which has immobilized inositol phosphate and does not have immobilized Ag, has slight antibacterial activity.

Figure 30:
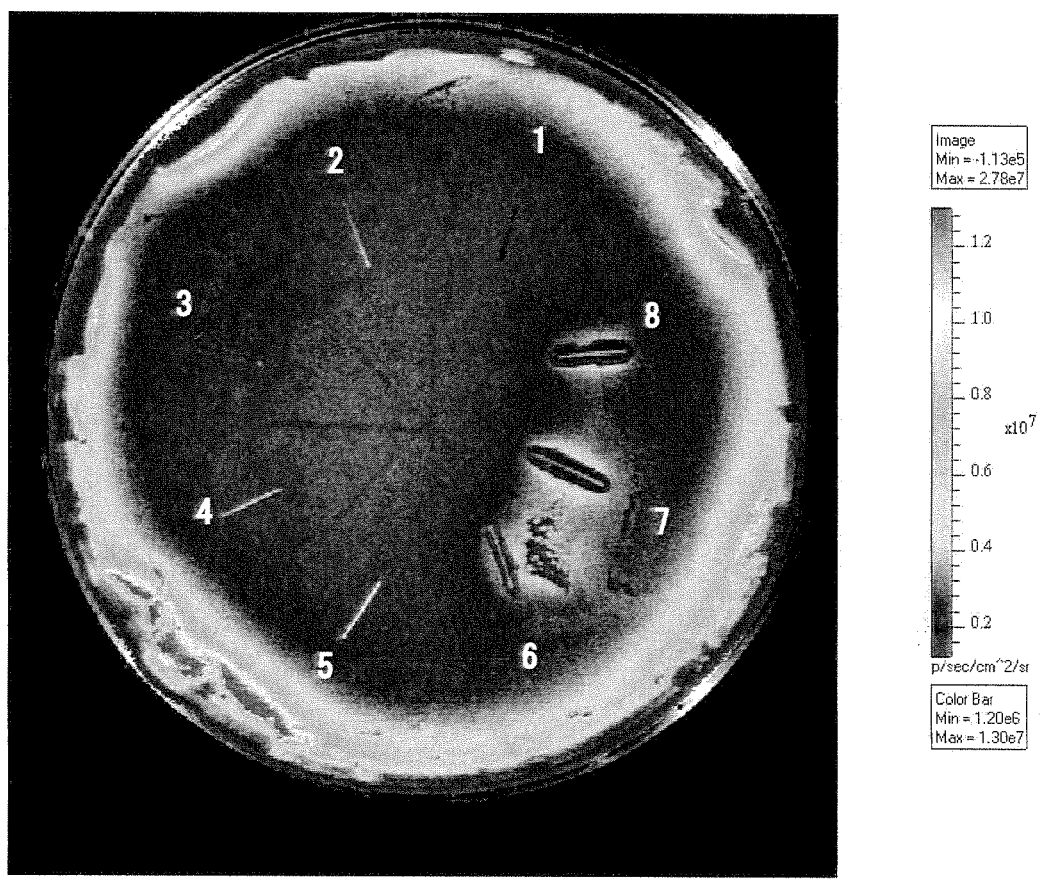
FIG. 30 is a bioluminescence (hereinafter referred to as bluc) image of the same entire Petri dish as in FIG. 29 using an imaging system IVIS® (manufactured by Xenogen Co.), where light emitted from luciferase-expressing *Staphylococcus aureus* is trapped high-sensitively.
Figure 32:
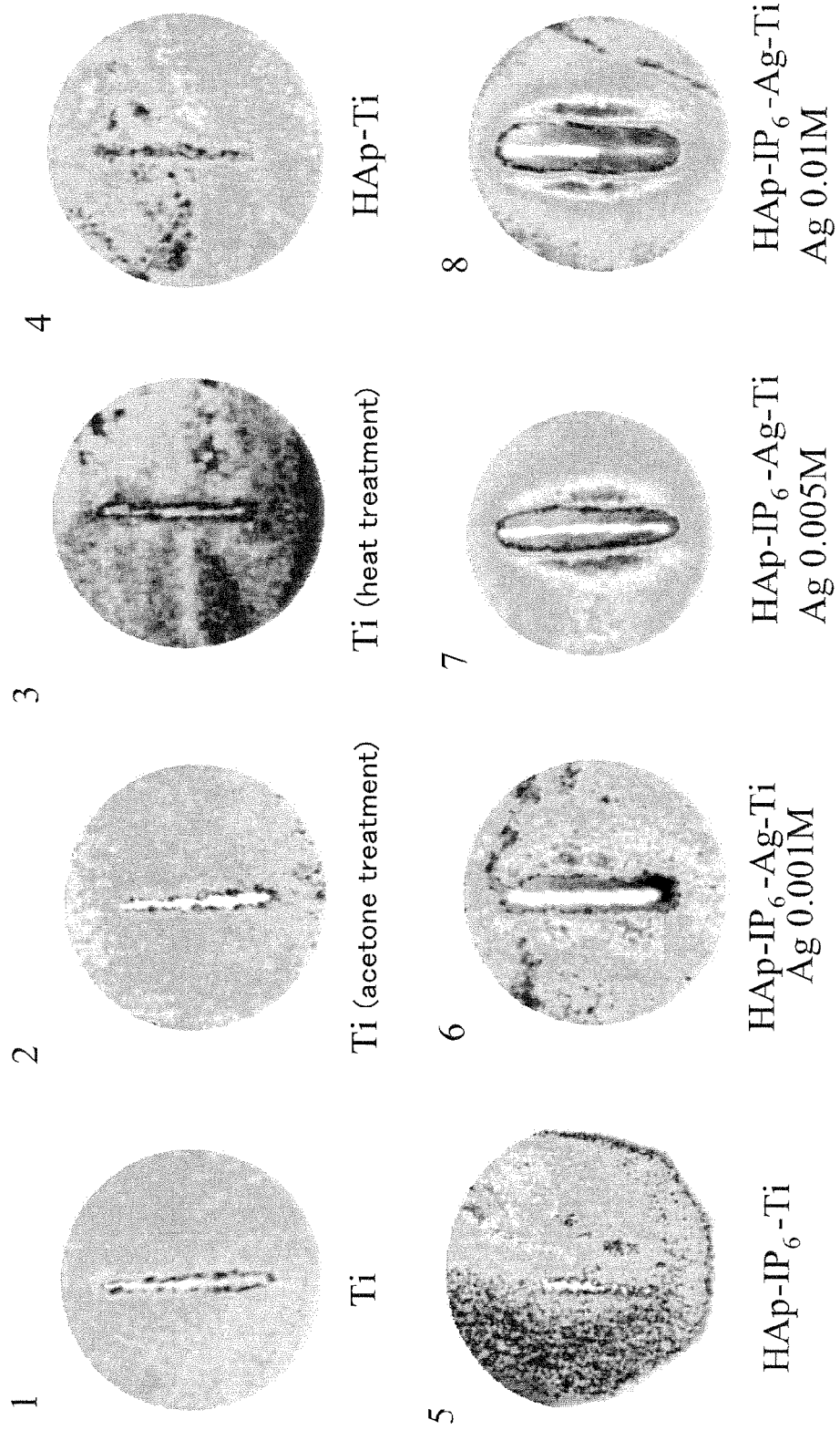
FIG. 32 shows bluc images (high magnification) of bacteria in a Petri dish, revealing results of an antibacterial activity of samples No. 1 to No. 8.

FIG. 30 is a bluc image obtained when high-sensitivity observation of trapping of light emitted from luciferase-expressing *Staphylococcus aureus* of the same entire Petri dish as in FIG. 29 using an imaging system IVIS® (manufactured by Xenogen Co.). FIG. 32 is bluc images around each of samples Nos. 1 to 8 of the Petri dish after culture. As is apparent from these drawings, the non-growing site (black) of bacteria is observed around the samples Nos. 6 to 8 with immobilized silver ions among samples Nos. 1 to 8 and the implants have strong antibacterial activity. It has also been recognized that the sample No. 5, which has immobilized inositol phosphate and does not have immobilized Ag, also has slight antibacterial activity.

With respect to the sample No. 7, assuming actual clinical application, the presence or absence of antibacterial activity was confirmed under various conditions. In actual clinical application, since the implant may be contacted with blood or abraded when inserted into the bone, some loss of Ag ion is anticipated.

Here, also with respect to the implant sample No. 7, the presence or absence of antibacterial activity was confirmed by conducting the Petri dish test with respect to the implant subjected to washing and rubbing. As the sample, four kinds of samples, such as an implant sample No. 7 (IP$_6$-Ag coating), a washed implant sample No. 7 (IP$_6$-Ag coating washed), a rubbed implant sample No. 7 (IP$_6$-Ag coating rubbed), and an implant sample No. 4 (HAp coating) for comparison.

Figure 33:
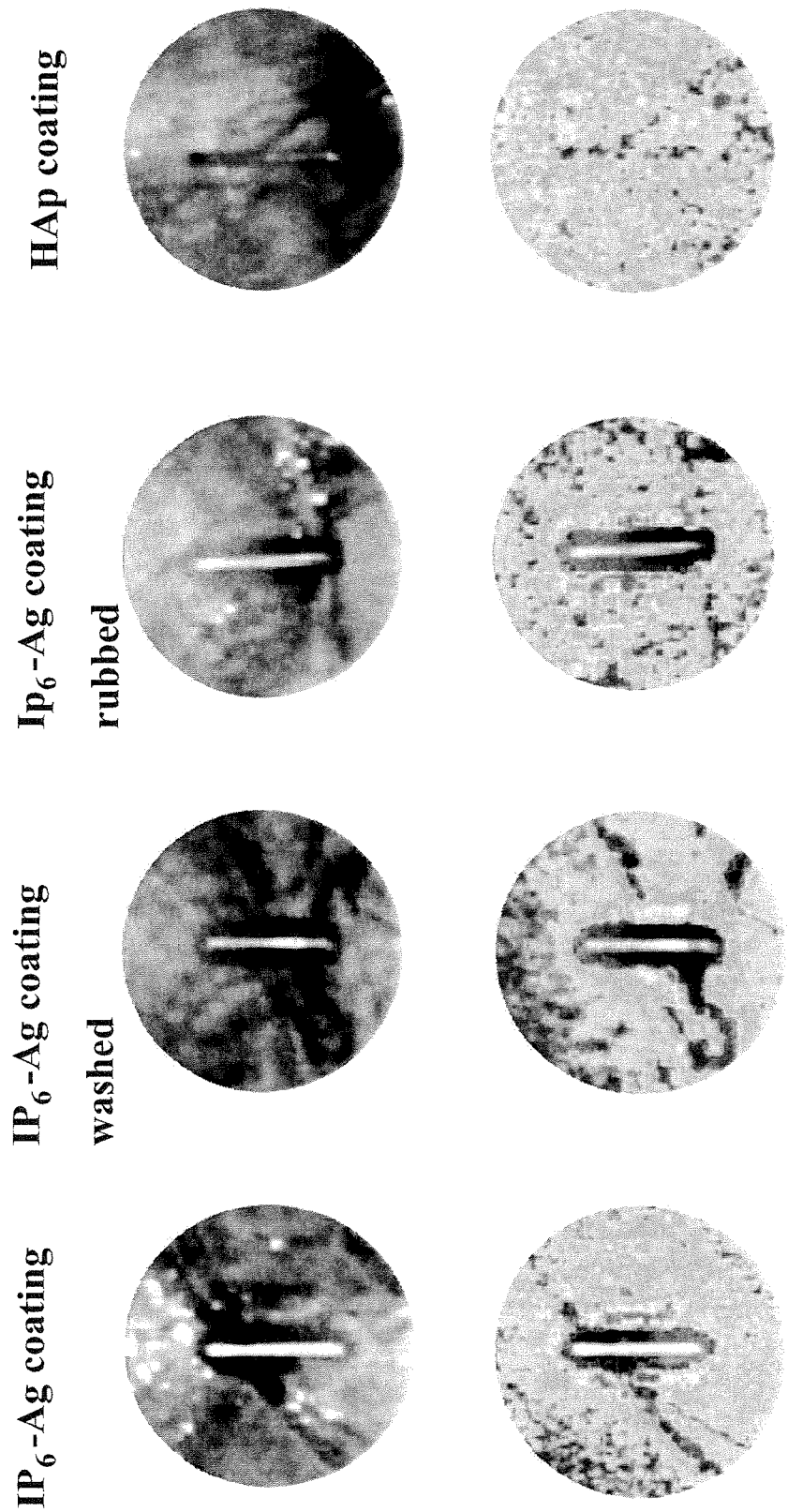
FIG. 33 shows phase-contrast and bluc images (high magnification), indicating results of an antibacterial activity test with respect to a non-treated implant sample No. 7, a washed implant sample No. 7, a rubbed implant sample No. 7, and an implant sample No. 4.

FIG. 33 shows results of a Petri dish test using the above four kinds of implants of interest, in which phase-contrast images around four kinds of implants are shown at the upper side, while bluc images are shown at the lower side.

As shown in FIG. 33, it is apparent that even when the implant sample No. 7 having strong antibacterial activity recognized is washed or rubbed, the non-growing site (black) of bacteria is observed around the implant and the antibacterial activity is sufficiently maintained. Therefore, it was confirmed that the implant sample No. 7 has durability and stability enough to withstand actual clinical application.

[In Vivo Antibacterial Activity Test-1]

Using BALB/c male adult mice, an osteomyelitis model was made.

As the implant, an implant sample No. 4 (HAp-Ti; hereinafter abbreviated to HAp) and a sample No. 7 (HAp-IP$_6$-Ag—Ti Ag 0.005M; hereinafter abbreviated to Ag+) among samples Nos. 1 to 8 were used, and these implants were implanted to the thighbone of a mouse.

Figure 34:
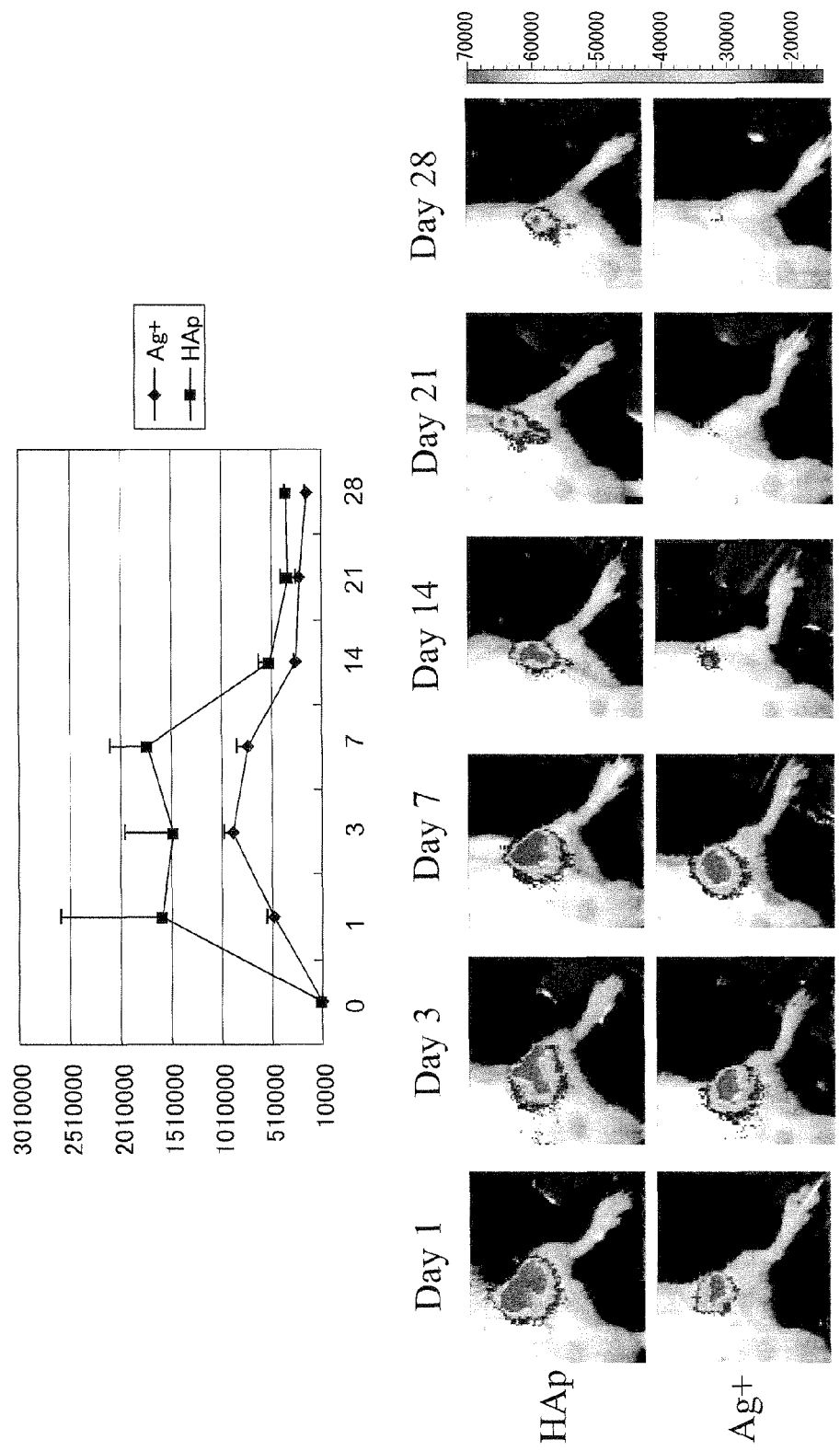
FIG. 34 shows a graph and bluc images, indicating time course results of a bacterial growth around an implant in a mouse in an in vivo test-1 in which implant samples No. 4 (HAp (control) group) and No. 7 ($Ag^+$ group) are implanted to the thighbone, followed by an injection of *Staphylococcus aureus*.
Figure 35:
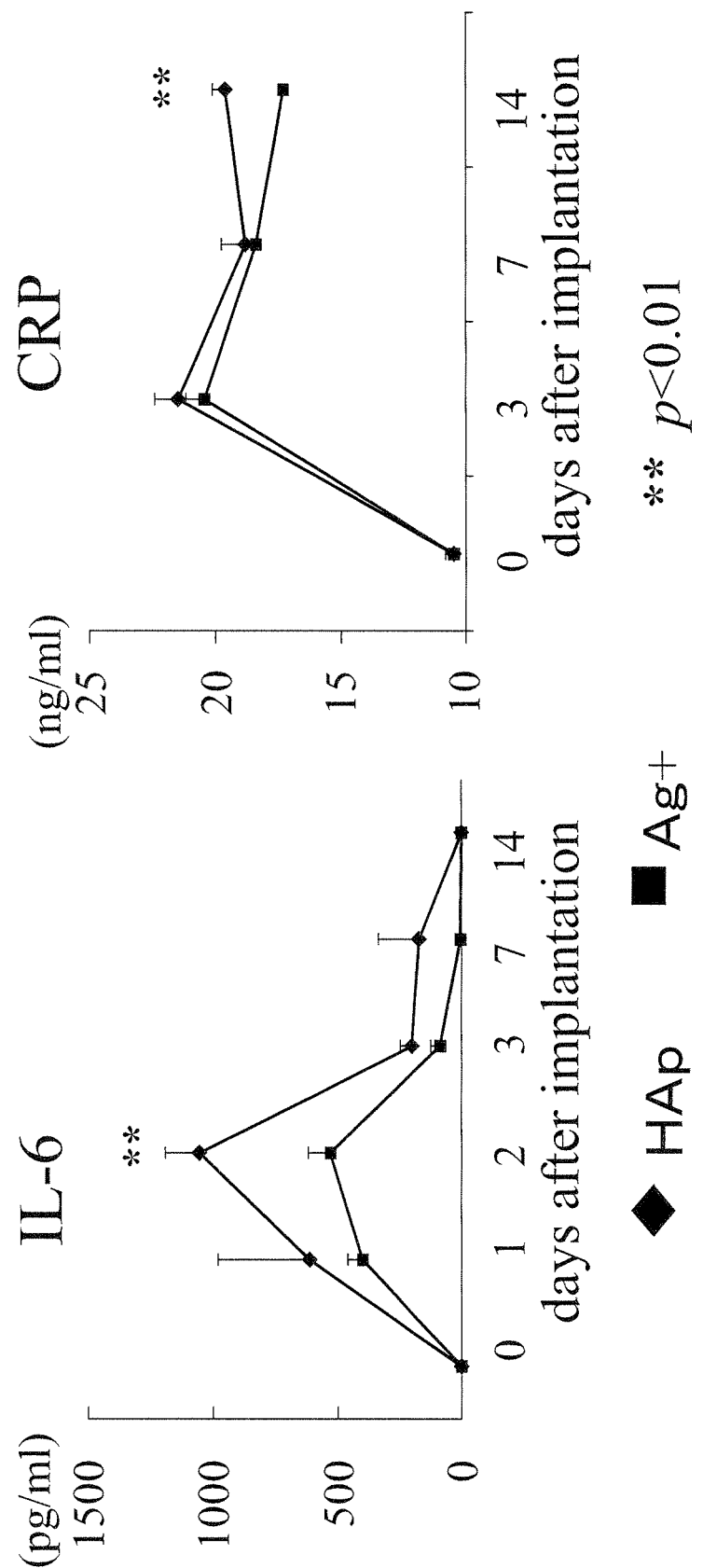
FIG. 35 is a graph showing time course changes of serum Interleukin 6 (IL-6: left drawing) and C-reactive protein (CRP: right drawing) levels in both HAp and Ag+ groups.

Luciferase-expressing *Staphylococcus aureus* was injected around the implanted implants. Using the above imaging system, high-sensitivity observation of trapping of light emitted from luciferase-expressing *Staphylococcus aureus* of this mouse was conducted for 28 days after implantation. The results are shown in FIG. 34. In addition, an inflammatory marker (Interleukin 6: IL-6 and C-reactive protein: CRP) in serum was measured with the lapse of time. The results are shown in FIG. 35. Furthermore, a histological assessment was also performed at 4 weeks after surgery. The results are shown in FIG. 36.

The graph at the upper side of FIG. 34 is a graph showing an average and a variation range of an emission intensity around the implanted site of a mouse implanted with either an implant HAp or Ag+ and also injected with the above bacteria (N=4 in both of HAp group and Ag+ group) measured on the 1st day, 3rd day, 7th day, 14th day, 21st day and 28th day after implantation using the above imaging system. The numerical value of the ordinate of the graph indicates the emission intensity (arbitrary intensity unit), while the numerical value of the abscissa indicates the number of days after implantation.

The images at the lower side of FIG. 34 are images showing a change with the lapse of time in the emission state of the bacteria implanted site of typical mice of both groups photographed on the 1st day, 3rd day, 7th day, 14th day, 21st day and 28th day using the above imaging system.

As is apparent from the results shown in FIG. 34, on the 1st day after implantation, in the HAp group, the emission intensity drastically increased and bacteria (luciferase-expressing *Staphylococcus aureus*) grew around the implant. In contrast, in the case of the Ag+ group, although the mission intensity increased, the emission intensity was statistically significantly lower than that of the HAp group.

On the 3rd day after implantation, in the case of mice of HAp group, a state of high emission intensity was maintained. In the case of mice of the Ag+ group, the emission intensity increased as compared with that measured on the 1st day, but was lower than that in the mouse of the HAp group.

On the 7th day after implantation, in the case of mice of the HAp group, the emission intensity increased as compared with that measured on the 3rd day. In contrast, in the case of the mouse of the Ag+ group, the emission intensity decreased as compared with that measured on the 3rd day. The emission intensity of the Ag+ group was statistically significantly low as compared with that in the HAp group.

On the 14th day after implantation, in both of the HAp group and the Ag+ group, the emission intensity decreased as compared with that measured on the 7th day due to natural immunity. The fact that bacteria die out by natural immunity is a phenomenon shown in a lot of past bacterial infection tests. In a comparison between both groups, the emission intensity measured on the 14th, 21st or 28th day in Ag+ group was lower than that in HAp group and decreased with the lapse of time. It is noteworthy that the emission intensity measured on the 28th day in the case of the Ag+ group was nearly identical to the background as shown in the image, in other words, bacteria died out almost completely.

As is apparent from the results shown in FIG. 34, the implant Ag+ of the present invention enabled inhibition of bacterial growth around the implant after implantation as compared with the implant HAp. The results proved that the implant according to the present invention exerts high antibacterial activity in vivo, and also exhibits strong antibacterial activity in the short term and can maintain antibacterial activity over a long period.

The graph of FIG. 35 is a graph showing an average and a variation range of Interleukin 6 (IL-6: left drawing) and C-reactive protein (CRP: right drawing) of a mouse implanted with either an implant HAp or Ag+ and also injected with the above bacteria (N=3 in both of HAp group and Ag+ group). Enzyme-linked immunosorbent assay (ELISA) method was used for measurement of the level of two inflammatory markers.

The numerical value of the ordinate of the graph indicates the concentration of each substance in serum, while the numerical value of the abscissa indicates the number of days after implantation.

As is apparent from the results shown in FIG. 35, in the acute stage on the 2nd day after implantation, the Ag+ group significantly exhibits a low increase in IL-6, compared with the HAp group, suggesting that the inflammation is remarkably suppressed in the Ag+ group. Also, the Ag+ group significantly exhibits a low increase in IL-6 even at each time point after implantation and approximately exhibits 0 pg/ml on the 7th day after implantation, which shows that inflammation is subsided. Although CRP levels increases in both groups until the 7th day after surgery since an influence of operation invasion is exerted, the Ag+ group significantly exhibits a low value on the 14th day after implantation, which shows that inflammation is subsided. These results are findings reflecting an image (FIG. 34) showing a change with the lapse of time, which is obtained by photographing the emission state of the bacteria implanted site of a mouse at each time after implantation using an imaging system. As is apparent from the above description, the Ag+ implant exhibits strong antibacterial activity not only in the acute stage after implantation, but also in the range from the sub-acute stage on the 14th day to the chronic stage.

FIG. 36 shows Hematoxylin and eosin (HE) staining of histological sections from thighbones collected at 4 weeks after implantation in both groups (HAp and Ag+ groups). In the HAp group, subperiosteal reactive bone peculiar to infection, so-called sequestration is remarkably observed and a normal bone structure is fractured, and inside the medullary cavity is filled with inflammatory cell (left drawing: HAp). In contrast, in the Ag+ group, surprisingly, an almost normal bone structure is exhibited and also inside the medullary cavity is filled with a lot of normal myeloid cells. As is apparent from the above results, the Ag+ implant exhibits strong antibacterial activity after implantation thereby to kill bacteria and to subside infection, thus remarkably suppressing an osteoclastic change due to infection.

[In Vivo Antibacterial Activity Test-2]

Similar to the [In vivo antibacterial activity test-1], an osteomyelitis model was made using BALE/c male adult mice.

As the implant, the sample No. 4 (HAp) and the sample No. 5 (HAp-$IP_6$-Ti; hereinafter abbreviated to $IP_6$) among the above samples Nos. 1 to 8 were used, and these implants were implanted to the thighbone of mice.

Luciferase-expressing *Staphylococcus aureus* was injected around the implants. Using the above imaging system, high-sensitivity observation of trapping of light emitted from luciferase-expressing *Staphylococcus aureus* of this mouse was conducted until the 1st to 28th day after implantation. The results are shown in FIG. 37.

The graph at the upper side of FIG. 37 is a graph showing an average and a variation range of an emission intensity around the implanted site of the mouse implanted with either an implant HAp or $IP_6$ and also injected with the above bacteria (N=6 in both of HAp group and $IP_6$ group) measured on the 1st day, 3rd day, 7th day, 14th day, 21st day and 28th day after implantation using the above imaging system. The numerical value of the ordinate of the graph indicates the emission intensity (arbitrary intensity unit), while the numerical value of the abscissa indicates the number of days after implantation.

The images at the lower side of FIG. 37 show a change with the lapse of time in the emission state of the bacteria-implanted site of typical mice of both groups photographed on the 1st day, 3rd day, 7th day, 14th day, 21st day and 28th day using the above imaging system.

As is apparent from the results shown in FIG. 37, on the 1st day after implantation, in the HAp group, the emission intensity drastically increased and bacteria (luciferase-expressing *Staphylococcus aureus*) grew around the implant. In $IP_6$ group, although the emission intensity increased, the emission intensity was slightly lower than that of the HAp group.

On the 3rd day after implantation, in the case of mice of HAp group, the emission intensity continuously increased. In the $IP_6$ group, the emission intensity increased but was lower than that in the HAp group.

At 7th day after implantation, in the HAp group, the emission intensity decreased as compared with that observed on the 3rd day but was still in a high level. In contrast, in the $IP_6$ group, the emission intensity drastically decreased as compared with that observed on the 3rd day. The emission intensity of the $IP_6$ group was statistically significantly low as compared with that in the HAp group.

On the 14th day to 21st day after implantation, although the emission intensity of both groups tended to decrease, the emission intensity of the mouse of the $IP_6$ group was still lower than that in the case of the mouse of the HAp group. At the times of 21st and 28th day after implantation, there was no significant change in the emission intensity of both groups, and the emission intensity of the $IP_6$ group was still lower than that in the case of the HAp group. It is noteworthy that the emission intensity measured on the 21st day or the subsequent day in the $IP_6$ group was nearly identical to the background as shown in the image, in other words, bacteria died out almost completely.

As is apparent from the results shown in FIG. 37, the implant $IP_6$ of the present invention had antibacterial activity similar to the implant Ag+ and enabled inhibition of bacterial growth around the implant after implantation as compared with the implant HAp. The results proved that the implant according to the present invention exerts high antibacterial activity in vivo, and also exhibits strong antibacterial activity over a long period.

INDUSTRIAL APPLICABILITY

According to the present invention, it is possible to provide an antibacterial medical equipment which has sufficient antibacterial activity in vivo and is excellent in compatibility with living tissues, and also can maintain antibacterial activity over a long period and has high safety.

The invention claimed is:

1. An antibacterial medical equipment characterized in that inositol phosphate is bonded to a calcium compound of a medical equipment whose surface is at least coated with a layer of the calcium compound, or a medical equipment comprising the calcium compound, wherein silver ions are bonded to the inositol phosphate, and inositol phosphate is directly bonded to a calcium compound of a medical equipment whose surface is at least coated with a layer of the calcium compound, or directly bonded to a medical equipment comprising the calcium compound, by bringing a medical equipment whose surface is at least coated with a layer of the calcium compound, or a medical equipment comprising the calcium compound, into contact with an aqueous solution of inositol phosphate to obtain the antibacterial medical equipment in which inositol phosphate is bonded to the calcium compound, and silver ions are chelated by the inositol phosphate by bringing the calcium compound into contact with an aqueous solution containing silver ions;

wherein the concentration of the aqueous solution containing silver ions is within a range from 0.001 to 0.01 mol/dm$^3$ to obtain the antibacterial medical equipment in which silver ions are bonded to the inositol phosphate;

wherein the calcium compound is hydroxyapatite;

wherein the inositol phosphate is phytic acid; and wherein the antibacterial medical equipment is an antibacterial implant.

2. The antibacterial medical equipment according to claim 1, wherein the antibacterial medical equipment is a tube, a catheter, a guide wire, a wire, a needle, an electrode, an intravascular ultrasonic wave probe, a dilator, a clip, an artificial membrane, an artificial fiber, an internal fixation material, a material for fixation of backbone, an intervertebral spacer, an artificial joint, an artificial organ, a pacemaker, a cardiac defibrillator, a lead, an otolaryngology-related medical material, a hemostatic material, a valve, a pump, a cannula, a filter, embolism substance, bone cement, a synthetic absorbable bone chip bonding material, a drain, a bag, a drape, an appliance for cosmetic surgery, a dental implant, or false teeth.

3. The antibacterial medical equipment according to claim 1, wherein the antibacterial medical equipment is an antibacterial implant so as to be transplanted.

4. The antibacterial medical equipment according to claim 1, wherein the thickness of the layer of hydroxyapatite is 1 μm or more.

5. The antibacterial medical equipment according to claim 1, wherein the time to bring the calcium compound into contact with the aqueous solution containing silver ions is 30 minutes or less.

6. The antibacterial medical equipment according to claim 1, wherein the time to bring the calcium compound into contact with the aqueous solution containing silver ions is within a range from 15 to 60 minutes.

7. The antibacterial medical equipment according to claim 1, wherein the time to bring the calcium compound into contact with the aqueous solution containing silver ions is within a range from 15 to 30 minutes.

8. The antibacterial medical equipment according to claim 1, wherein the medical equipment is made of metallic materials, synthetic resins, calcium compounds, or ceramics.

* * * * *